United States Patent
Kellinger et al.

(10) Patent No.: US 12,134,766 B2
(45) Date of Patent: Nov. 5, 2024

(54) METHODS FOR GENERATING CIRCULAR NUCLEIC ACID MOLECULES

(71) Applicant: Element Biosciences, Inc., San Diego, CA (US)

(72) Inventors: Matthew Kellinger, San Diego, CA (US); Sinan Arslan, San Diego, CA (US); Michael Previte, San Diego, CA (US); Junhua Zhao, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/153,268

(22) Filed: Jan. 11, 2023

(65) Prior Publication Data

US 2023/0167434 A1    Jun. 1, 2023

Related U.S. Application Data

(63) Continuation of application No. 17/320,042, filed on May 13, 2021, which is a continuation of application No. PCT/US2019/061871, filed on Nov. 15, 2019.

(60) Provisional application No. 62/767,943, filed on Nov. 15, 2018.

(51) Int. Cl.
  C12N 15/10    (2006.01)
  C12N 9/12     (2006.01)
  C12Q 1/6869   (2018.01)

(52) U.S. Cl.
  CPC .......... *C12N 15/1068* (2013.01); *C12N 9/12* (2013.01); *C12N 9/1241* (2013.01); *C12Q 1/6869* (2013.01)

(58) Field of Classification Search
  None
  See application file for complete search history.

(56) References Cited

U.S. PATENT DOCUMENTS

| | | |
|---|---|---|
| 6,284,497 B1 | 9/2001 | Sabanayagam et al. |
| 7,211,390 B2 | 5/2007 | Rothberg et al. |
| 7,709,197 B2 | 5/2010 | Drmanac |
| 7,754,429 B2 | 7/2010 | Rigatti et al. |
| 7,767,400 B2 | 8/2010 | Harris |
| 7,897,344 B2 | 3/2011 | Dahl et al. |
| 7,901,891 B2 | 3/2011 | Drmanac |
| 7,910,302 B2 | 3/2011 | Drmanac et al. |
| 7,910,354 B2 | 3/2011 | Drmanac et al. |
| 7,960,120 B2 | 6/2011 | Rigatti et al. |
| 8,236,505 B2 | 8/2012 | Rigatti et al. |
| 8,399,196 B2 | 3/2013 | Hoser |
| 8,415,099 B2 | 4/2013 | Drmanac et al. |
| 8,431,348 B2 | 4/2013 | Rigatti et al. |
| 8,518,640 B2 | 8/2013 | Drmanac et al. |
| 8,551,702 B2 | 10/2013 | Drmanac et al. |
| 8,592,150 B2 | 11/2013 | Drmanac et al. |
| 8,617,811 B2 | 12/2013 | Drmanac |
| 8,637,650 B2 | 1/2014 | Cherkasov et al. |
| 8,673,562 B2 | 3/2014 | Drmanac |
| 8,765,379 B2 | 7/2014 | Drmanac |
| 8,765,381 B2 | 7/2014 | Rigatti et al. |
| 8,951,731 B2 | 2/2015 | Drmanac et al. |
| 8,999,642 B2 | 4/2015 | Sabot et al. |
| 9,023,769 B2 | 5/2015 | Drmanac et al. |
| 9,029,103 B2 | 5/2015 | Rigatti et al. |
| 9,222,132 B2 | 12/2015 | Drmanac |
| 9,228,228 B2 | 1/2016 | Drmanac et al. |
| 9,238,834 B2 | 1/2016 | Drmanac et al. |
| 9,267,172 B2 | 2/2016 | Drmanac et al. |
| 9,267,173 B2 | 2/2016 | Rigatti et al. |
| 9,328,382 B2 | 5/2016 | Drmanac et al. |
| 9,624,489 B2 | 4/2017 | Sabot et al. |
| 9,637,785 B2 | 5/2017 | Drmanac |
| 9,650,673 B2 | 5/2017 | Drmanac et al. |
| 9,663,822 B2 | 5/2017 | Luo et al. |
| 9,708,649 B2 | 7/2017 | Saito et al. |
| 9,944,924 B2 | 4/2018 | Rigatti et al. |
| 9,944,984 B2 | 4/2018 | Drmanac et al. |
| 10,100,350 B2 | 10/2018 | Breslauer et al. |
| 10,125,392 B2 | 11/2018 | Drmanac |
| 10,221,452 B2 | 3/2019 | Rigatti et al. |
| 10,227,647 B2 | 3/2019 | Ke et al. |
| 10,233,490 B2 | 3/2019 | Stapleton et al. |
| 10,329,613 B2 | 6/2019 | Rigatti et al. |
| 10,351,909 B2 | 7/2019 | Drmanac et al. |
| 10,590,464 B2 | 3/2020 | Boutell et al. |
| 10,704,094 B1 | 7/2020 | Arslan et al. |

(Continued)

FOREIGN PATENT DOCUMENTS

| | | |
|---|---|---|
| GB | 2584801 A | 12/2020 |
| WO | WO-0183826 A2 | 11/2001 |

(Continued)

OTHER PUBLICATIONS

Takahashi et al., "Real-time single-molecule observations of T7 Exonuclease activity in a microflow channel," Anal. Biochem. 2014, 457:24-30. (Year: 2014).*
Smith, "Restriction Endonuclease Digestion of DNA," Methods Mol. Biol. 1993, 18:427-431. (Year: 1993).*
Berki et al., Advanced Fluorescent Polymer Probes for the Site-Specific Labeling of Proteins in Live Cells Using the HaloTag Technology. ACS Omega 4: 12841-12847 (2019).
Dubber et al., Solid Phase Synthesis and Multivalent Glycoconjugates on a DNA Synthesizer. Bioconjugate Chem 14: 239-246 (2003).
Duret et al., Labeling of native proteins with fluorescent RAFT polymer probes: Application to the detection of a cell surface protein using flow cytometry. Polym. Chem. 9: 1857-1868 (2018).

(Continued)

*Primary Examiner* — Kaijiang Zhang
(74) *Attorney, Agent, or Firm* — WILSON SONSINI GOODRICH & ROSATI

(57) ABSTRACT

Provided herein are methods for generating circular nucleic acid molecules and circular nucleic acid libraries. The methods can be used to generate clonal populations of target nucleic acid molecules for downstream applications such as sequencing.

20 Claims, 6 Drawing Sheets

Specification includes a Sequence Listing.

(56) References Cited

U.S. PATENT DOCUMENTS

| | | |
|---|---|---|
| 10,768,173 B1 | 9/2020 | Arslan et al. |
| 10,787,573 B2 | 9/2020 | Zheng et al. |
| 10,876,148 B2 | 12/2020 | Zhou et al. |
| 10,919,033 B2 | 2/2021 | Ren et al. |
| 10,982,280 B2 | 4/2021 | Arslan et al. |
| 11,053,540 B1 | 7/2021 | Chen et al. |
| 11,060,138 B1 | 7/2021 | Chen et al. |
| 11,118,214 B2 | 9/2021 | Matthiesen et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,261,489 B2 | 3/2022 | Chen et al. |
| 11,287,422 B2 | 3/2022 | Previte et al. |
| 11,339,433 B2 | 5/2022 | Chen et al. |
| 11,365,444 B2 | 6/2022 | Chen et al. |
| 11,408,032 B2 | 8/2022 | Chen et al. |
| 11,426,732 B2 | 8/2022 | Guo et al. |
| 11,427,855 B1 | 8/2022 | Arslan et al. |
| 11,447,582 B2 | 9/2022 | Brown et al. |
| 11,459,608 B2 | 10/2022 | Chen et al. |
| 11,535,892 B1 | 12/2022 | Arslan et al. |
| 11,781,185 B2 | 10/2023 | Arslan et al. |
| 11,795,504 B2 | 10/2023 | Chen et al. |
| 2010/0105052 A1 | 4/2010 | Drmanac et al. |
| 2011/0059865 A1 | 3/2011 | Smith et al. |
| 2011/0111975 A1 | 5/2011 | Schneider et al. |
| 2016/0289750 A1 | 10/2016 | Landegren et al. |
| 2016/0357173 A1 | 12/2016 | Foschini et al. |
| 2016/0369334 A1 | 12/2016 | Zhou et al. |
| 2016/0376647 A1 | 12/2016 | Travers et al. |
| 2017/0009287 A1 | 1/2017 | Brastaad et al. |
| 2017/0152554 A1 | 6/2017 | Drmanac et al. |
| 2018/0023119 A1 | 1/2018 | Adey et al. |
| 2019/0292594 A1 | 9/2019 | Rigatti et al. |
| 2020/0115748 A1 | 4/2020 | Drmanac et al. |
| 2020/0149095 A1 | 5/2020 | Arslan et al. |
| 2020/0179921 A1 | 6/2020 | Arslan et al. |
| 2020/0182866 A1 | 6/2020 | Arslan et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332430 A1 | 10/2021 | Arslan et al. |
| 2021/0373000 A1 | 12/2021 | Arslan et al. |
| 2021/0387184 A1 | 12/2021 | Guo et al. |
| 2022/0136047 A1 | 5/2022 | Chen et al. |
| 2022/0349002 A1* | 11/2022 | Patterson et al. .... C12Q 1/6837 |
| 2023/0235392 A1 | 7/2023 | Arslan et al. |

FOREIGN PATENT DOCUMENTS

| | | |
|---|---|---|
| WO | WO-02059372 A2 | 8/2002 |
| WO | WO-2005123957 A2 | 12/2005 |
| WO | WO-2006138257 A2 | 12/2006 |
| WO | WO-2009045344 A2 | 4/2009 |
| WO | WO-2012003374 A2 | 1/2012 |
| WO | WO-2014020154 A1 | 2/2014 |
| WO | WO-2014171898 A2 | 10/2014 |
| WO | WO-2015188192 A2 | 12/2015 |
| WO | WO-2016028887 A1 | 2/2016 |
| WO | WO-2017176679 A1 | 10/2017 |
| WO | WO-2018045109 A1 | 3/2018 |
| WO | WO-2019033062 A2 | 2/2019 |
| WO | WO-2019079593 A1 | 4/2019 |
| WO | WO-2019241305 A1 | 12/2019 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022094332 A1 | 5/2022 |
| WO | WO-2022164989 A2 | 8/2022 |
| WO | WO-2022266470 A1 | 12/2022 |
| WO | WO-2023004014 A1 | 1/2023 |
| WO | WO-2022266462 A3 | 5/2023 |
| WO | WO-2023096672 A1 | 6/2023 |
| WO | WO-2023096674 A1 | 6/2023 |
| WO | WO-2023107719 A2 | 6/2023 |
| WO | WO-2023196924 A2 | 10/2023 |
| WO | WO-2023205707 A2 | 10/2023 |

OTHER PUBLICATIONS

Favier et al., Synthesis on N-acryloxysuccinimide copolymers by RAFT polymerization, as reactive building blocks with full control of composition and molecular weights. Polymer 45: 7821-7830 (2004).

Gebeyehu et al., Novel biotinylated nucleotide—analogs for labeling and colorimetric detection of DNA. Nucleic Acids Research 15(11): 4513-4534 (1987).

Head et al., Library construction for next-generation sequencing: Overviews and challenges. Biotechniques 56(2): 61-77 (2014).

Lorenz: Polymerase chain reaction: basic protocol plus troubleshooting and optimization strategies. J Vis Exp. 63):e3998:1-14 doi:10.3791/3998 (2012).

PCT/US19/61871 International Search Report and Written Opinion dated May 21, 2020.

PCT/US2021/033191 International Search Report and Written Opinion dated Nov. 1, 2021.

Snyder. Classification of the solvent properties of common liquids. Journal of Chromatography A 92(2):223-30 (1974).

Deng et al., DNA-Sequence-Encoded Rolling Circle Amplicon for Single-Cell RNA Imaging. Chem 4:1373-1386 (2018).

Neumann et al., Padlock Probe Assay for Detection and Subtyping of Seasonal Influenza. Clinical Chemistry 64(12):1704-1712 (2018).

* cited by examiner

SEQUENCE LISTING

```
Sequence total quantity: 5
SEQ ID NO: 1            moltype = AA  length = 631
FEATURE                 Location/Qualifiers
source                  1..631
                        mol_type = protein
                        organism = Escherichia virus N15
SEQUENCE: 1
MSKVKIGELI NTLVNEVEAI DASDRPQGDK TKRIKAAAAR YKNALFNDKR KFRGKGLQKR    60
ITANTFNAYM SRARKRFDDK LHHSFDKNIN KLSEKYPLYS EELSSWLSMP TANIRQHMSS   120
LQSKLKEIMP LAEELSNVRI GSKGSDAKIA RLIKKYPDWS FALSDLNSDD WKERRDYLYK   180
LFQQGSALLE ELHQLKVNHE VLYHLQLSPA ERTSIQQRWA DVLREKKRNV VVIDYPTYMQ   240
SIYDILNNPA TLFSLNTRSG MAPLAFALAA VSGRRMIEIM FQGEFAVSGK YTVNFSGQAK   300
KRSEDKSVTR TIYTLCEAKL FVELLTELRS CSAASDFDEV VKGYGKDDTR SENGRINAIL   360
AKAFNPWVKS FFGDDRRVYK DSRAIYARIA YEMFFRVDPR WKNVDEDVFF MEILGHDDEN   420
TQLHYKQFKL ANFSRTWRPE VGDENTRLVA LQKLDDEMPG FARGDAGVRL HETVKQLVEQ   480
DPSAKITNST LRAFKFSPTM ISRYLEFAAD ALGQFVGENG QWQLKIETPA IVLPDEESVE   540
TIDEPDDESQ DDELDEDEIE LDEGGGDEPT EEEGPEEHQP TALKPVFKPA KNNGDGTYKI   600
EFEYDGKHYA WSGPADSPMA AMRSAWETYY S                                 631

SEQ ID NO: 2            moltype = DNA  length = 56
FEATURE                 Location/Qualifiers
misc_feature            1..56
                        note = Description of Unknown: Enzyme recognition nucleic
                        acid sequence
source                  1..56
                        mol_type = other DNA
                        organism = unidentified
SEQUENCE: 2
tatcagcaca caatagtcca ttatacgcgc gtataatggg caattgtgtg ctgata         56

SEQ ID NO: 3            moltype = DNA  length = 56
```

```
FEATURE              Location/Qualifiers
misc_feature         1..56
                     note = Description of Unknown: Enzyme recognition nucleic
                     acid sequence
source               1..56
                     mol_type = other DNA
                     organism = unidentified
SEQUENCE: 3
tatcagcaca caattgccca ttatacgcgc gtataatgga ctattgtgtg ctgata       56

SEQ ID NO: 4         moltype = DNA  length = 52
FEATURE              Location/Qualifiers
misc_feature         1..52
                     note = Description of Artificial Sequence: Synthetic
                     oligonucleotide
source               1..52
                     mol_type = other DNA
                     organism = synthetic construct
SEQUENCE: 4
tatcagcaca caatagtcca ttatacgtat aatggactat tgtgtgctga ta           52

SEQ ID NO: 5         moltype = DNA  length = 60
FEATURE              Location/Qualifiers
misc_feature         1..60
                     note = Description of Artificial Sequence: Synthetic
                     oligonucleotide
source               1..60
                     mol_type = other DNA
                     organism = synthetic construct
SEQUENCE: 5
tatcagcaca caattgccca ttatacgcgc gcgcgtataa tgggcaattg tgtgctgata   60
```

METHODS FOR GENERATING CIRCULAR NUCLEIC ACID MOLECULES

CROSS-REFERENCE

This application is a continuation of U.S. patent application Ser. No. 17/320,042, filed May 13, 2021, which is a continuation of International Application No. PCT/US2019/061871, filed Nov. 15, 2019, which claims the benefit of U.S. Provisional Application No. 62/767,943, filed on Nov. 15, 2018, each of which is incorporated herein by reference in its entirety.

SEQUENCE LISTING

The instant application contains a Sequence Listing which has been submitted electronically in XML format and is hereby incorporated by reference in its entirety. Said XML copy, created on Jan. 11, 2023, is named "Element 52933-715302.xml" and is 7,696 bytes in size.

BACKGROUND

Next-generation sequencing (NGS) techniques have become a powerful tool for acquiring sequencing data used in molecular biology techniques, taxonomy, agriscience, medical diagnostics, and the development of new therapies. For example, sequencing-by-synthesis (SBS) methods are used to extend a growing polynucleotide chain, while analyzing the identity of matching complementary nucleotides that are incorporated. However, additional methods to increase the sensitivity, accuracy, scalability, and cost efficiency of these methods are needed.

SUMMARY

Provided herein are methods for generating circular nucleic acid molecules and circular nucleic acid libraries for next-generation sequencing.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1A:
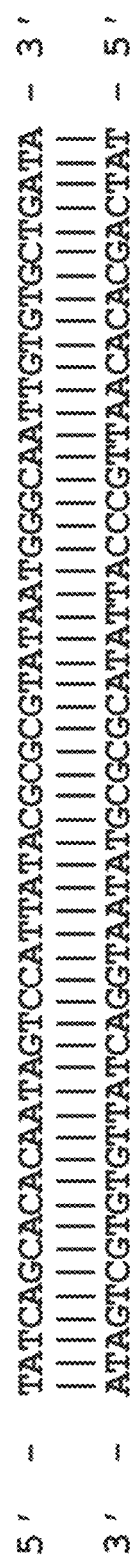
FIG. 1A depicts an example of a double-stranded enzyme recognition nucleic acid molecule.

Provided herein are methods for generating circular nucleic acid molecules and circular nucleic acid libraries. Some of such methods create circular nucleic acid molecules (e.g., circular DNA molecules) without using a nucleic acid ligase. Rather, some methods disclosed herein use an enzyme that identifies a nucleic acid having a target enzyme recognition sequence, cleaves the enzyme recognition nucleic acid molecule at a target site so as to generate an end having a 5' and 3' exposed cleavage ends, rejoins 5' and 3' cleavage ends of a single exposed end at the target site to form a single linear molecule from the cleaved 5' and 3' ends. When this reaction is performed on both ends of a double-stranded nucleic acid molecule having a target molecule added at each end, the result is a circular nucleic acid molecule.

A number of enzymes or enzyme combinations are compatible with this reaction. Often, the enzyme is a protelomerase. One type of protelomerase is TelN protelomerase, such as that from *E. coli* phage N1. One type of the enzyme recognizes one or more enzyme recognition nucleic acid molecules attached to random linear double-stranded nucleic acid molecules to create a circular nucleic acid library suitable for sequencing. Some of the libraries generated require clonal amplification of the circular nucleic acid molecules before sequencing process. The use of the enzyme has several advantages to other nucleic acid library preparation methods.

One of such advantages is that the circular nucleic acid molecule contains both the forward and reverse sequences of a target nucleic acid molecule or nucleic acid region of interest. If the circular nucleic acid molecule contains both the forward and reverse sequences, it eliminates the process to synthesize a complementary strand to obtain "paired-end" information. In some embodiments, both 5' flanking regions to the target nucleic acid molecule contains different sequences and can be hybridized with different sequencing primers to obtain paired-end sequencing reads. Such method eliminates the process to resynthesize and linearize DNA strands between Read 1 and Read 2 to obtain paired end information. Some of the methods disclosed herein simplify a library preparation workflow by removing several reagents used for resynthesis and decrease overall runtime.

Another advantage is that some of the methods disclosed herein are more efficient than other nucleic acid library preparation methods. Currently, common method for nucleic acid circularization involve blunt end or splinted ligation. These methods suffer from several drawbacks: (1) multiple steps (e.g., high temperature annealing of nucleic acid splint followed by low temperature ligation); (2) inefficiency (e.g., ligation rarely goes to completion in a realistic amount of time amenable for nucleic acid sequence library preparation); (3) incomplete reaction (e.g., ligation-based circularization rarely results in complete circularization of library strands resulting in loss of a significant fraction of the initial target nucleic acid). Methods disclosed herein, on the other hand, allow library generation in as few as 5 minutes or less, such as 1 hour, 45 minutes, 30 minutes, 25 minutes, 20 minutes, 15 minutes, 10 minutes, 9 minutes, 8 minutes, 7 minutes, 6 minutes, 5 minutes, or no more than 5 minutes, or anytime period within the range defined by this list. Alternatives may run longer. Consistent with this rapid library generation, library generation as disclosed herein is optionally performed isothermally, such as in PCR compatible or other regularly available enzyme buffers.

Definitions

Unless defined otherwise, all technical and scientific terms used herein have the same meaning as commonly understood to one of ordinary skill in the art to which this disclosure belongs. It is to be understood that the foregoing general description and the following detailed description are exemplary and explanatory only and are not restrictive of any subject matter claimed.

As used herein and in the appended claims, the singular forms "a," "and," and "the" include plural referents unless the context clearly dictates otherwise. Also, the use of "and" means "and/or" unless stated otherwise. Similarly, "comprise," "comprises," "comprising" "include," "includes," and "including" are interchangeable and not intended to be limiting.

The term "about" or "approximately" can mean within an acceptable error range for the particular value as determined by one of ordinary skill in the art, which will depend in part on how the value is measured or determined, e.g., the limitations of the measurement system. For example, "about" can mean plus or minus 10%, per the practice in the art. Alternatively, "about" can mean a range of plus or minus 20%, +plus or minus 10%, plus or minus 5%, or plus or minus 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed. Also, where ranges and/or subranges of values are provided, the ranges and/or subranges can include the endpoints of the ranges and/or subranges.

A "nucleic acid molecule" is a linear polymer of two or more nucleotides joined by covalent internucleosidic linkages, or variant or functional fragments thereof. In naturally occurring examples of these, the internucleoside linkage is typically a phosphodiester bond. However, other examples optionally comprise other internucleoside linkages, such as phosphorothiolate linkages and may or may not comprise a phosphate group. The nucleic acid molecules include double- and single-stranded DNA, as well as double- and single-stranded RNA, DNA:RNA hybrids, peptide-nucleic acids (PNAs) and hybrids between PNAs and DNA or RNA, and also include known types of modifications. The nucleic acid molecule can optionally be attached to one or more non-nucleotide moieties such as labels and other small molecules, large molecules such proteins, lipids, sugars, and solid or semi-solid supports, for example through either the 5' or 3' end.

The term "nucleotide" as used herein refers to a molecule comprising an aromatic base, a sugar, and a phosphate. Canonical or non-canonical nucleotides are consistent with use of the term. The phosphate in some instances comprises a monophosphate, diphosphate, or triphosphate, or corresponding phosphate analog. Occasionally, "nucleotide" is used informally to refer to a base in a nucleic acid molecule.

Nucleic acids may optionally be attached to one or more non-nucleotide moieties such as labels and other small molecules, large molecules (such as proteins, lipids, sugars, e/c.), and solid or semi-solid supports, for example through covalent or non-covalent linkages with either the 5' or 3' end of the nucleic acid. Labels include any moiety that is detectable using any of a variety of detection methods known to those of skill in the art, and thus renders the attached oligonucleotide or nucleic acid similarly detectable. Some labels emit electromagnetic radiation that is optically detectable or visible. Alternately or in combination, some labels comprise a mass tag that renders the labeled oligonucleotide or nucleic acid visible in mass spectral data, or a redox tag that renders the labeled oligonucleotide or nucleic acid detectable by amperometry or voltammetry. Some labels comprise a magnetic tag that facilitates separation and/or purification of the labeled oligonucleotide or nucleic acid. The nucleotide or polynucleotide is often not attached to a label, and the presence of the oligonucleotide or nucleic acid is directly detected.

The term "barcode" as used herein refers to a natural or synthetic nucleic acid sequence comprised by a polynucleotide allowing for unambiguous identification of the polynucleotide and other sequences comprised by the polynucleotide having said barcode sequence. The number of different barcode sequences theoretically possible can be directly dependent on the length of the barcode sequence; e.g., if a DNA barcode with randomly assembled adenine, thymidine, guanosine and cytidine nucleotides can be used, the theoretical maximal number of barcode sequences possible can be 1,048,576 for a length of ten nucleotides, and can be 1,073,741,824 for a length of fifteen nucleotides.

As used herein, the terms "DNA hybridization" and "nucleic acid hybridization" are used interchangeably, and are intended to cover any type of nucleic acid hybridization, e.g., DNA hybridization, RNA hybridization, etc., unless otherwise specified. Hybridization may occur through Watson-Crick basepairing, Hoogsteen pairing, G-loop pairing, or any mechanism that is or may be known in the art for the specific and/or ordered noncovalent interaction of bases within two or more nucleic acid strands. "Hybridization" may comprise interactions between segments of a single molecule, two molecules, or more than two molecules of a nucleic acid In some embodiments, the methods and compositions of the present disclosure comprise a label, such as a fluorescent label or a fluorophore. In some embodiments, the label is a fluorophore. Exemplary fluorescent moieties which may serve as fluorescent labels or fluorophores include, but are not limited to, fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-2-(3-{1-[6-(2,5-dioxopyrrolidin-1-yl)oxy)-6-oxohexyl)-2((1E,3E)-5-((E)-1-(6-((2,5-dioxopyrrolidin-1-yl)oxy)-6-oxohexyl)-3,3-dimethyl-5-indolin-2-ylidene}penta-1,3-dien-1-yl)-3,3-dimethyl-3H-indol-1-ium or 1-(6-((2,5-dioxopyrrolidin-1-yloxy)-6-oxohexyl)-2-1E,3E)-5-((E)-1-(6-((2,5-dioxopyrrolidin-1-yl)oxy)-6-oxo-hexyl)-3,3-dimethyl-5-sulfoindolin-2-ylidene}penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

Organic Solvent: An organic solvent is a solvent or solvent system comprising carbon-based or carbon-containing substance capable of dissolving or dispersing other substances. An organic solvent may be miscible or immiscible with water.

Polar Solvent: A polar solvent as included in the hybridization composition described herein is a solvent or solvent system comprising one or more molecules characterized by the presence of a permanent dipole moment, i.e., a molecule having a spatially unequal distribution of charge density. A polar solvent may be characterized by a dielectric constant of 20, 25, 30, 35, 40, 45, 50, 55, 60 or higher or by a value or a range of values incorporating any of the aforementioned values. For example, a polar solvent may have a dielectric constant of higher than 100, higher than 110, higher than 111, or higher than 115. A polar solvent as described herein may comprise a polar aprotic solvent. A polar aprotic solvent as described herein may further contain no ionizable hydrogen in the molecule. In addition, polar solvents or polar aprotic solvents may be preferably substituted in the context of the presently disclosed compositions with a strong polarizing functional groups such as nitrile, carbonyl, thiol, lactone, sulfone, sulfite, and carbonate groups so that the underlying solvent molecules have a dipole moment. Polar solvents and polar aprotic solvents can be present in both aliphatic and aromatic or cyclic form. In some embodiments, the polar solvent is acetonitrile.

The term "support" includes any solid or semisolid article on which reagents such as nucleic acids can be immobilized. Nucleic acids may be immobilized on the solid support by any method including but not limited to physical adsorption, by ionic or covalent bond formation, or combinations thereof. A solid support may include a polymeric, a glass, or a metallic material. Examples of solid supports include a membrane, a planar surface, a microtiter plate, a bead, a filter, a test strip, a slide, a cover slip, and a test tube, means any solid phase material upon which an oligomer is synthesized, attached, ligated or otherwise immobilized. A support can optionally comprise a "resin", "phase", "surface," "substrate," "coating," and/or "support." A support may comprise organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Surfaces may be planar, substantially planar, or non-planar. Supports may be porous or non-porous, and may have swelling or non-swelling characteristics. A support can be shaped to comprise one or more wells, depressions or other containers, vessels, features or locations. A plurality of supports may be configured in an array at various locations. A support is optionally addressable (e.g., for robotic delivery of reagents), or by detection means including scanning by laser illumination and confocal or deflective light gathering. An amplification support (e.g., a bead) can be placed within or on another support (e.g., within a well of a second support).

As used herein, fluorescence is 'specific' if it arises from fluorophores that are annealed or otherwise tethered to the surface, such as through a nucleic acid having a region of reverse complementarity to a corresponding segment of an oligo on the surface and annealed to said corresponding segment. This fluorescence is contrasted with fluorescence arising from fluorophores not tethered to the surface through such an annealing process, or in some cases to background florescence of the surface.

As used herein, a liquid phase is considered continuous if any portion of the liquid phase is in fluid contact or communication with any other portion of the liquid body. For example, a liquid phase may be considered continuous if no portion is entirely subdivided or compartmentalized or otherwise entirely physically separated from the rest of the liquid body. In some cases, a liquid phase may be flowable. In some cases, a continuous liquid phase is not within a gel or matrix. In other cases, a continuous liquid phase may be within a gel or matrix. For example, a continuous liquid phase may occupy pores, spaces or other interstices of a solid or semisolid support.

As used herein, "paired end" information refers to genetic sequence information pertaining to both the forward and reverse strands of a double stranded nucleic acid molecule or nucleic acid segment. A paired-end read or paired-end sequencing thus refers to the determination of the sequence of both the forward and the reverse strand. This determination may be made directly and may in some embodiments be made without reference to the sequence of a known complementary strand.

Generating Circular Nucleic Acid Molecules

Methods disclosed herein comprise generating a circular nucleic acid molecule. Some of the methods comprise providing at least two double-stranded enzyme recognition nucleic acid molecules, at least one double-stranded target nucleic acid molecule, and at least one adapters; joining the two double-stranded enzyme recognition nucleic acid molecules to the one double-stranded target nucleic acid molecule to form a joint double-stranded nucleic acid molecule; and contacting the joint double-stranded nucleic acid molecule to an enzyme to form the circular nucleic acid molecule. Some of the joint double-stranded nucleic acid molecules comprise at least one adapter between the double-stranded enzyme recognition nucleic acid molecule and the double-stranded target nucleic acid molecule.

Adapters are nucleic acid molecules with known or unknown sequence. Adapters are variously attached to the 3'end, 5'end, or both ends of a nucleic acid molecule (e.g. target nucleic acid). Adapters comprise known sequences and/or unknown sequences. Double-stranded and single-stranded adapters are both compatible with various embodiments of the present disclosure. Some of the adapters comprise a barcode (e.g. unique identifier sequence). In some cases, adapters are amplification adapters. The amplification adapters attach to a target nucleic acid and help the amplification of the target nucleic acid. For example, a given amplification adapter comprises one or more of: a primer binding site, a unique identifier sequence, a non-unique identifier sequence, and a surface binding site. In some cases, a target nucleic acid molecule attached with at least one amplification adapter is immobilized on a surface.

Often, an amplification primer hybridizes to the adapter to be extended using the target nucleic acid molecule as a template in an amplification reaction. Unique identifiers in an adapter are optionally used to label the amplicons. Some of the adapters are sequencing adapters. Some of the sequencing adapters attach to a target nucleic acid and help the sequencing of the target nucleic acid molecule. For example, a sequencing adapter comprises one or more of: a sequencing primer binding site, a unique identifier site, a non-unique identifier site, and a surface binding site. Some of the target nucleic acid molecules attached with a sequencing adapter are immobilized on a surface on a sequencer. Some of the sequencing primers hybridize to the adapter to be extended using the target nucleic acid molecule as a template in a sequencing reaction. Unique identifiers in an adapter are used in some cases to label the sequence reads of different target sequences, thus allowing high-throughput sequencing of a plurality of target nucleic acid molecules.

Adapters recognize or are complementary to a primer, such as a universal primer. Alternately or in combination, some adapters are specific to a sequencing method. Some of the adapters are single-stranded oligonucleotide added to the ends of the double-stranded target nucleic acid molecule before the joining. Some of the adapters are double-stranded oligonucleotide added to the ends of other nucleic acid molecules. Some of the adapters are synthesized to have blunt ends to both terminals. Some of the adapters are synthesized to have sticky end at one end and blunt end at the other. Some of the adapters are synthesized to have sticky end to both terminals.

As mentioned above, adapters optionally comprise a universal primer site, a surface binding site, or an index site. Some of the adapters comprise at least two of the universal primer site, the surface binding site, and the index site. Some of the adapters comprise the universal primer site, the surface binding site, and the index site. Some of the universal primer sites comprise one or more universal primers. Some of the universal primers are PCR/sequencing primers that bind to a sequence found in a plurality of plasmid cloning vectors. Some of the universal primer sites comprise one or more amplification primers. Some of the universal primers comprise one or more nucleic acid molecules that are complementary to one or more amplification primers. Some of the universal primer sites comprise one or more nucleic acid molecules that are complementary to one or more universal primers. Some of the surface binding sites are complementary to binding regions covalently attached to a surface. Some of the surface binding sites are configured to immobilize the circular nucleic acid molecules to the surface. After immobilization, the circular nucleic acid molecules are amplified.

Index sites comprise one or more index primers. Some of the index primers enable multiple samples to be sequenced together on the same instrument flow cell or chip. One of such index primer has at least 6 bases, 7 bases, 8 bases, 9 bases, 10 bases or greater. Smaller index primers are also contemplated. Some of the adapters contain single or dual sample indexes depending on the number of libraries combined and the level of accuracy desired. Some of the adapters contain unique molecular identifiers to increase error correction and accuracy. Some of the unique molecular identifiers are short sequences that incorporate a unique barcode onto each molecule within a given sample library. Some of the unique molecular identifiers reduce the rate of false-positive variant calls and increase sensitivity of variant detection. Some of the adapters containing the unique molecular identifiers are xGen Dual Index UMI adapters. Some of the adapters comprise platform-specific sequences for fragment recognition by a sequencer. Some of the platform-specific sequences comprise the P5 and P7 sequences enabling library fragments to bind to the flow cells.

In some embodiments, the enzyme cleaves the double-stranded enzyme recognition nucleic acid molecule and, after the cleavage, rejoins cleavage ends of the double-stranded enzyme recognition nucleic acid molecule. In some embodiments, the enzyme cleaves the double-stranded enzyme recognition nucleic acid molecule and, after the cleavage, rejoins cleavage ends of the double-stranded enzyme recognition nucleic acid molecule to form hairpin structures at one or both of the double stranded exposed ends resulting from cleavage of the molecule.

Figure 1B:
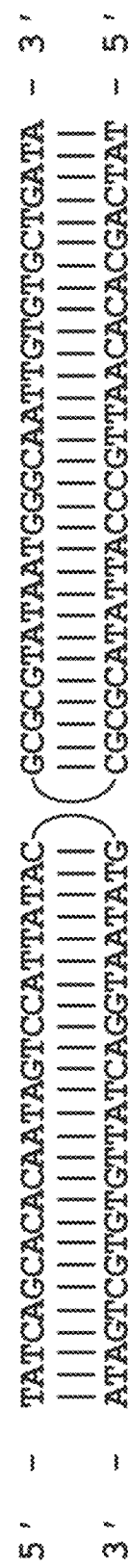
FIG. 1B depicts an example of the double-stranded enzyme recognition nucleic acid molecule after enzyme treatment.

One type of enzyme compatible with the disclosure herein is a protelomerase. One type of the protelomerase is TelN protelomerase. One of the double-stranded enzyme recognition nucleic acid molecule is a double-stranded enzyme recognition DNA sequence. FIG. 1A describes one of the double-stranded enzyme recognition DNA molecules. In some cases, TelN protelomerase exhibits specificity for the double-stranded enzyme recognition DNA molecules of FIG. 1A. One function of the TelN protelomerase is to catalyze the double-stranded enzyme recognition DNA molecule of FIG. 1A and result in an internal strand hydrolysis and ligation event. One result of the internal strand hydrolysis and ligation event is to produce the product demonstrated in FIG. 1B.

In some embodiments, the joining is carried out by a polymerase during polymerization reactions. One type of the polymerase is a nucleic acid polymerase. One or more primers, whether in soluble form or attached to a support, are incubated with a polymerization or extension reaction mix, which optionally comprises any one or more reagents such as enzyme, dNTPs and buffers. In some cases, the one or more primer is extended through an extension. In some cases, the extension is achieved by an enzyme with polymerase activity or other extension activity, such as a polymerase. The enzyme can optionally have other activities including 3'-5' exonuclease activity (proofreading activity) and/or 5'-3' exonuclease activity. Alternatively, in some embodiments, the enzyme can lack one or more of these activities. In an embodiment the polymerase has strand-displacing activity. Examples of useful strand-displacing polymerases include Bacteriophage D29 DNA polymerase and Bst DNA polymerase. In some cases, the enzyme is active at elevated temperatures, e.g., at least 45° C., at least 50° C., at least 60° C., at least 65° C., at least 70° C., at least 75° C., or at least 85° C.

An exemplary polymerase is Bst DNA Polymerase (Exonuclease Minus), a 67 kDa*Bacillus stearothermophilus* DNA Polymerase protein (large fragment), exemplified in accession number 2BDP_A, which has 5'-3' polymerase activity and strand displacement activity but lacks 3'-5' exonuclease activity. Other polymerases include Taq DNA polymerase I from *Therms aquaticus* (exemplified by accession number 1TAQ), Eco DNA polymerase I from *Echerichia coli* (accession number P00582), Aea DNA polymerase I from Aquifex aeolicus (accession number 067779), or functional fragments or variants thereof, e.g., with at least 80%, 85%, 90%, 95% or 99% sequence identity at the nucleotide level.

Some of the adapters are inserted between the double-stranded enzyme recognition nucleic acid molecule and the double-stranded target nucleic acid molecule by a transposase. One type of the transposase is an enzyme that binds to the end of a transposon and catalyzes the movement of the transposon to another part of a nucleic acid molecule. Such movement is performed by a cut and paste mechanism or a replicative transposition mechanism. One type of the transposase is Tn5 transposase. Some of the adapters are ligated to the double-stranded target nucleic acid molecule by a ligase before the joining. One type of the ligase is a DNA ligase.

Figure 2:
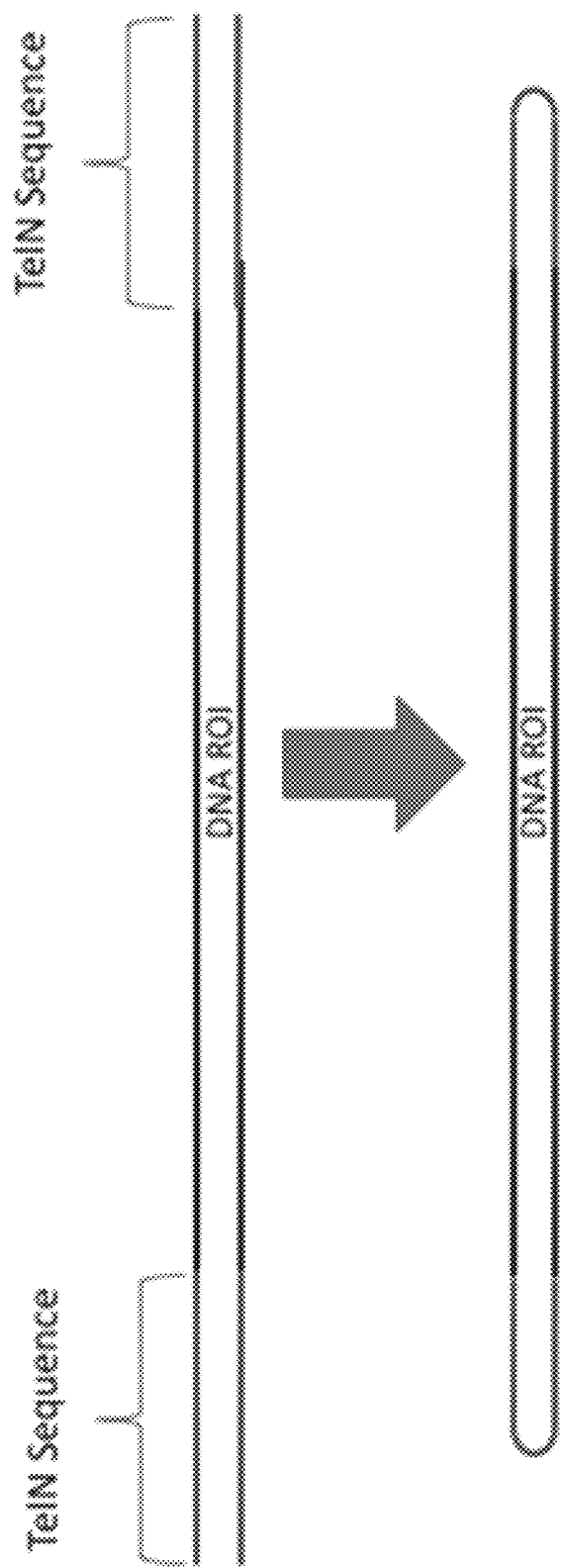
FIG. 2 depicts an example of a method for generating a circular nucleic acid molecule.

One type of the target double-stranded nucleic acid molecule is a target double-stranded DNA molecule. In the illustrated example of FIG. 2, to create a circular DNA molecule with the target double-stranded DNA molecule, a double-stranded enzyme recognition DNA molecule is inserted flanking the target double-stranded DNA molecule. Both ends of the target double-stranded DNA molecule are inserted with the double-stranded enzyme recognition DNA molecule. Then the TelN protelomerase catalyzes the double-stranded enzyme recognition DNA molecule on both ends of the target double-stranded DNA molecule to produce a circularized DNA molecule with the target double-stranded DNA molecule circularized, as demonstrated in FIG. 2. The circular DNA molecule produced herein can be used as a template to grow monoclonal DNA populations that are spatially resolved and attached covalently to a surface. In some embodiments, the methods disclosed herein ensure that the target nucleic acid molecules are appropriately spaced in the support to favor formation of monoclonal populations of amplified nucleic acid molecule without substantial cross-contamination between different clonal populations.

Library Preparation

The methods described herein are readily incorporated into the library sequencing methods (e.g., synthesis by sequencing). Provided herein are methods for generating a circular nucleic acid sequence library. Some of methods comprise fragmenting a double-stranded nucleic acid sample to form a plurality of double-stranded nucleic acid fragments; joining a plurality of enzyme recognition nucleic acid molecules to the plurality of double-stranded nucleic acid fragments to form a plurality of joint double-stranded nucleic acid molecules; and contacting at least one joint double-stranded nucleic acid molecule to an enzyme to form a circular nucleic acid molecule, thereby generating a circular nucleic acid library from the double-stranded nucleic acid sample.

At least some of the plurality of joint double-stranded nucleic acid molecules have at least one enzyme recognition nucleic acid molecule on each end. In some embodiments, the enzyme cleaves the enzyme recognition nucleic acid molecule to form a double-stranded enzyme recognition nucleic acid fragment in one joint-double stranded nucleic acid molecule, and rejoins cleavage ends of the double-stranded enzyme recognition nucleic acid fragment. In some cases, after the enzyme cleaves the enzyme recognition nucleic acid molecule, the enzyme rejoins the cleavage ends of the enzyme recognition nucleic acid molecule to form hairpin structures.

In some embodiments, the circular nucleic acid library comprises at least 1, 10, 100, 1000, 10000, 100000 or more than 100000 distinct circular nucleic acid molecules. Some of the circular nucleic acid libraries comprise between about 1 to 100000, 10 to 10000, or 100 to 1000 circular nucleic acid molecules with distinct sequences.

Fragmenting variously comprises at least one of shearing, sonicating, restriction digesting, sequence specific endonuclease treatment, sequence-independent endonuclease treatment and chemical digesting, as well as other shearing approaches. Various shearing options include acoustic shearing, point-sink shearing, and needle shearing. In some steps, the restriction digesting is the intentional sequence specific breaking of nucleic acid molecules. One type of the restriction digesting is an enzyme-based treatment to fragment the double-stranded nucleic acid molecules either by the simultaneous cleavage of both strands, or by generation of nicks on each strand of the double-stranded nucleic acid molecules to produce double-stranded nucleic acid molecules breaks. One type of sonication subjects nucleic acid molecules to acoustic cavitation and hydrodynamic shearing by exposure to brief periods of sonication. As one type of shearing, the acoustic shearing transmits high-frequency acoustic energy waves to nucleic acid molecules. As another type of shearing, the point-sink shearing uses a syringe pump to create hydrodynamic shear forces by pushing a nucleic acid library through a small abrupt contraction. As yet another type of shearing, the needle shearing creates shearing forces by passing DNA libraries through small gauge needle. After the fragmenting, some of the double-stranded nucleic acid fragments contain a region of a nucleic acid sequence with at least about 20, 30, 40, 50, 60, 70, 80, 90, 100, 110, 120, 130, 140, 150, 160, 170, 180, 190, 200, 225, 250, 300, 350, 400, 450, 500, 550, 600 bp or more. In some cases, after the fragmenting, some of the double-stranded nucleic acid fragments contain a region of a nucleic acid sequence with less than about 20.

In some embodiments, the fragmenting further comprises end repair, sticky end generation, and overhang generation. One type of the overhang generation comprises 5' end generation. One type of the overhang generation comprises 3' end generation. Some of the steps, such as end repair, sticky end generation, or overhang generation are performed in a tube. Some of the steps, such as such as end repair, sticky end generation, or overhang generation are performed with a solution containing the double-stranded nucleic acid fragments, end repair buffer, and end repair enzyme.

One type of the enzyme comprises a first enzyme that cleaves the enzyme recognition nucleic acid molecule to form a double-stranded enzyme recognition nucleic acid fragment in the one joint-double stranded nucleic acid molecule and a second enzyme that rejoins cleavage ends of the double-stranded enzyme recognition nucleic acid fragment. Another type of the enzyme is a protelomerase. One type of the protelomerase is TelN protelomerase.

One of the double-stranded enzyme recognition nucleic acid molecule is a double-stranded enzyme recognition DNA molecule. One of the double-stranded enzyme recognition DNA molecules is described in FIG. 1A. In some embodiments, TelN protelomerase exhibits specificity for the double-stranded enzyme recognition DNA molecule of FIG. 1A. In this situation, TelN protelomerase catalyzes the double-stranded enzyme recognition DNA molecule and results in an internal strand hydrolysis and ligation event. Such internal strand hydrolysis and ligation even produce the product demonstrated in FIG. 1B.

In some embodiments, the joining is carried out by a nucleic acid polymerase during polymerization reactions. One or more primers, whether in soluble form or attached to a support, are incubated with a polymerization or extension reaction mix, which optionally comprises any one or more reagents such as enzyme, dNTPs and buffers. In some cases, the one or more primer is extended through an extension. In some cases, the extension is achieved by an enzyme with polymerase activity or other extension activity, such as a polymerase. The enzyme can optionally have other activities including 3'-5' exonuclease activity (proofreading activity) and/or 5'-3' exonuclease activity. Alternatively, in some embodiments the enzyme can lack one or more of these activities. In an embodiment the polymerase has strand-displacing activity. Examples of useful strand-displacing polymerases include Bacteriophage 029 DNA polymerase and Bst DNA polymerase. In some cases, the enzyme is active at elevated temperatures, e.g., at least 45° C., at least 50° C., at least 60° C., at least 65° C., at least 70° C., at least 75° C., or at least 85° C.

Some of the joint double-stranded nucleic acid molecules comprise at least one adapter between the enzyme recognition nucleic acid molecule and the double-stranded nucleic acid fragment. Some of the adapters are single-stranded oligonucleotide added to the ends of the double-stranded nucleic acid fragment. Some of the adapters are double-stranded oligonucleotide added to the ends of other nucleic acid molecules. Some of the adapters are synthesized to have blunt ends to both terminals. Some of the adapters are synthesized to have sticky end at one end and blunt end at the other. Some of the adapters are synthesized to have sticky end to both terminals. Some of the adapters comprise a universal primer site, a surface binding site, or an index site. The universal primer site, the surface binding site, and the index site are described elsewhere herein. Some of the adapters contain unique molecular identifiers to provide the highest levels of error correction and accuracy. Some of the unique molecular identifiers are short sequences that incorporate a unique barcode onto each molecule within a given sample library. Some of the unique molecular identifiers reduce the rate of false-positive variant calls and increase sensitivity of variant detection. Some of the adapters containing the unique molecular identifiers are xGen Dual Index UMI adapters. Some of the adapters comprise platform-specific sequences for fragment recognition by a sequencer. Some of the platform-specific sequences comprise the P5 and P7 sites enabling library fragments to bind to the flow cells. The adapters, the universal primer site, the surface binding site, and the index site are described elsewhere herein.

Some of the adapters are inserted between the double-stranded enzyme recognition nucleic acid molecule and the double-stranded target nucleic acid molecule by a transposase. One type of the transposase is an enzyme that binds to the end of a transposon and catalyzes the movement of the transposon to another part of a nucleic acid molecule. Such movement is performed by a cut and paste mechanism or a replicative transposition mechanism. One type of the transposase is Tn5 transposase. Some of the adapters are ligated to the double-stranded nucleic acid molecule by a ligase before the joining.

Some methods disclosed herein comprise separating the plurality of circular nucleic acid molecules before any amplification steps. One type of the separating is performed with separation material. One type of the separation material comprises a plurality of beads. Another type of the separation material comprises an array, such as an array of wells or an array of beads. Some of the separation material comprises a column, such as a packed column, a size-exclusion column, a magnetic column, or any combination thereof. In some embodiments, the separation material comprises a bead, a capillary, a plate, a membrane, a wafer, a well, a plurality of any of these, an array of any of these, or any combination thereof. Some of the separation material positively selects a circular nucleic acid molecule of interest by associating the circular nucleic acid molecule of interest with the separation material. Some of the separation material negatively selects for a circular nucleic acid molecule of interest by associating other circular nucleic acid molecules of a sample with the separation material.

Instead of joining the plurality of enzyme recognition nucleic acid molecules to the plurality of double-stranded nucleic acid fragments through ligation, some of the methods disclosed herein join the plurality of enzyme recognition nucleic acid molecules to the plurality of double-stranded nucleic acid fragments through PCR. Such methods comprise preparing a plurality of primers, wherein a given primer of the plurality of primers comprises one strand of the enzyme recognition nucleic acid molecule; annealing the given primer to a single strand of a given double-stranded nucleic acid fragment; extending the given primer to generate a reverse strand of the single strand of the given double-stranded nucleic acid fragment; and creating a forward strand complementary to the reverse strand, wherein the forward strand comprises the single strand of the given double-stranded nucleic acid fragment and the given primer. Some of the forward strands are amplified.

Some of the double-stranded target nucleic acid molecules are from nucleic acid molecules in general, e.g., DNA or derived from a biological sample or synthetic RNA molecules (e.g., dsRNA), and are able to be processed using any of a variety of techniques known to those of skill in the art prior to performing the joining. Examples of such processing steps include, but are not limited to, extraction and purification steps to separate the nucleic acid molecules from other components of the sample, shearing, cleavage, digestion, or fragmentation steps to obtain a collection or library of nucleic acid template molecules of a desired average length, polyadenylation steps, adapter ligation steps to attach adapter sequences to a first and/or second end of the nucleic acid template molecules, library amplification steps, target sequence capture and/or purification steps, or any combination thereof.

Figure 3:
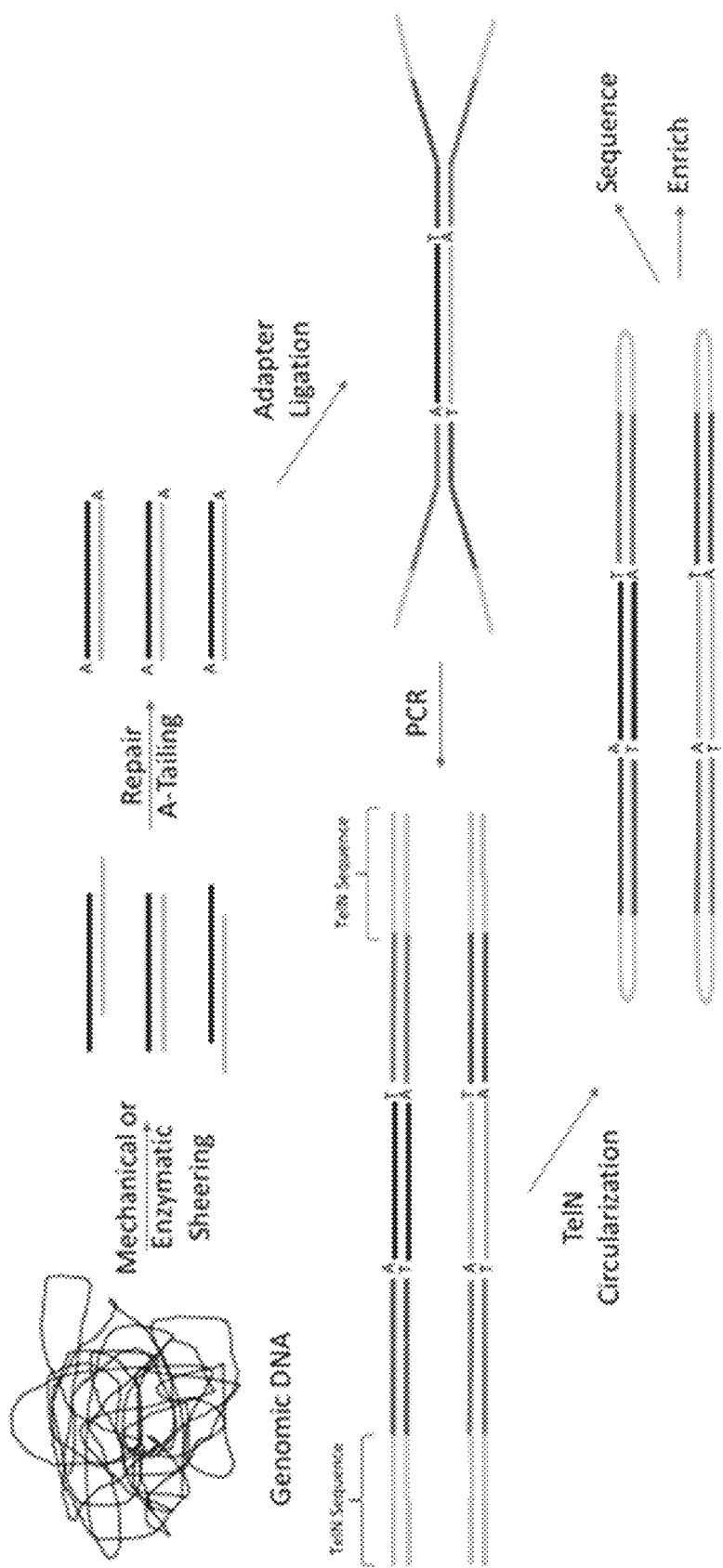
FIG. 3 depicts an example of a workflow of generating a circular nucleic acid library.

In an exemplary library preparation workflow, the double-stranded enzyme recognition nucleic acid sequence is added by adapter ligation or PCR, if the desired libraries are PCR-free. The exemplary workflow is described in FIG. 3. The exemplary workflow comprises the following steps.

In step one, a double-stranded nucleic acid molecule is sheared mechanically or enzymatically into a plurality of double-stranded nucleic acid fragments. The plurality of double-stranded nucleic acid fragments are 100-5000 bp fragments.

In step two, the plurality of double-stranded nucleic acid fragments are modified. The modification comprises repairing and A-tailing by polymerase. The process of A tailing is performed by adding adenine to 3' end of each of the plurality of double-stranded nucleic acid fragments.

In step three, one or more adapters are ligated onto the A-tailed double-stranded nucleic acid fragments. The one or more adapters are ligated onto the both ends of A-tailed double-stranded nucleic acid fragments. The one or more adapters comprise a universal primer site, a surface binding site, a P5 site, a P7 site, or an index site. The double-stranded enzyme recognition nucleic acid molecules are inserted at both ends of the adapter-ligated A—tailed double-stranded nucleic acid fragments to form joint double-stranded nucleic acid molecules.

In step four of some exemplary workflows, PCR is used to amplify the joint double-stranded nucleic acid molecules.

In step five, TelN protelomerase is added to the reaction to generate the circular nucleic acid sequence library. The circular nucleic acid sequence library is then purified by Solid Phase Reversible Immobilization (SPRI). The purification process uses SPRI magnetic beads. The magnetic beads are coated with carboxyl groups that can reversibly bind to the circular nucleic acid sequences. The magnetic beads are formulated to specifically bind to the circular nucleic acid sequences and purify out unwanted excess primers, adapter dimers, and salts and enzymes from a wide variety of reactions.

If less PCR cycling is desired, the PCR step (step four) is replaced with an end-elongation step. The end elongation step anneals primers to the joint double-stranded nucleic acid molecules and extends in both 3' directions completing the joint double-stranded nucleic acid molecules without introducing significant PCR bias.

Hairpin Ligation

Provided herein are methods for generating one or more circular nucleic acid molecules. The method comprises: denaturing a double-stranded enzyme recognition nucleic acid molecule to form two single-stranded enzyme recognition nucleic acid molecules; joining each of the two single-stranded enzyme recognition nucleic acid molecules to each end of a target double-stranded nucleic acid molecule to form a joint nucleic acid molecule, wherein, after the joining, each of the two single-stranded enzyme recognition nucleic acid molecules takes a form of a hairpin; denaturing the joint nucleic acid molecule; hybridizing the two single-stranded enzyme recognition nucleic acid molecules in the joint nucleic acid molecule to form the double-stranded enzyme recognition nucleic acid molecule in the joint nucleic acid molecule; and contacting the joint nucleic acid molecule with an enzyme, wherein the enzyme binds to the double-stranded enzyme recognition nucleic acid molecule to form two circular nucleic acid molecules. In some embodiments, one of the two circular nucleic acid molecules contains a reverse strand that is complementary to a forward strand in another one of the two circular nucleic acid molecules.

In some embodiments, the enzyme cleaves the double-stranded enzyme recognition nucleic acid molecule and, after the cleavage, rejoins cleavage ends of the double-stranded enzyme recognition nucleic acid molecule. In some embodiments, the enzyme cleaves the double-stranded enzyme recognition nucleic acid molecule and, after the cleavage, rejoins cleavage ends of the double-stranded enzyme recognition nucleic acid molecule to form hairpin structures. One type of the enzyme is a protelomerase. One type of the protelomerase is TelN protelomerase. The TelN protelomerase is described elsewhere herein.

Some of the joint nucleic acid molecules comprise at least one adapter between the enzyme recognition nucleic acid molecule and the target double-stranded nucleic acid molecule. Some of the adapters are described elsewhere herein. Some of the adapters comprise a universal primer site, a surface binding site, or an index site. The universal primer site, the surface binding site, and the index site are described elsewhere herein. Some of the adapters contain unique molecular identifiers, which are described elsewhere herein. Some of the adapters comprise the P5 and P7 sites enabling library fragments to bind to the flow cells. In some embodiments, the joint nucleic acid molecules do not comprise any adapter between the enzyme recognition nucleic acid molecule and the target double-stranded nucleic acid molecule.

Figure 4:
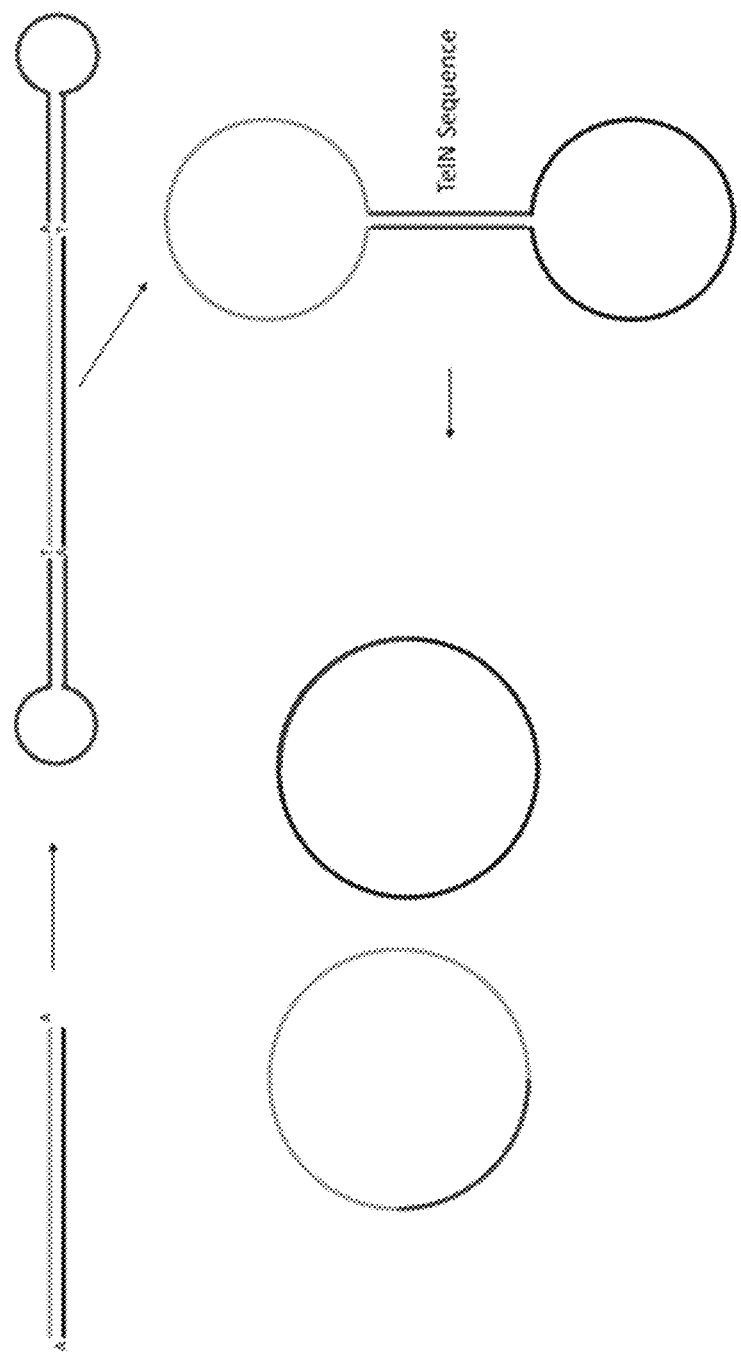
FIG. 4 depicts an example of a method for generating circular nucleic acid molecules.

As illustrated in FIG. 4, two complementary single-stranded enzyme recognition nucleic acid molecule are placed the on each end of a target double-stranded nucleic acid molecule by hairpin ligation. A hairpin is a nucleic acid molecule containing both a region of single stranded molecule (a loop region) and regions of self-complementary molecule such that an intra-molecular duplex is formed under hybridizing conditions. Next, an intramolecular circularization is performed to create double-stranded enzyme recognition nucleic acid molecule. Next, TelN protelomerase catalyzes the double-stranded enzyme recognition nucleic acid molecule to produce two independent circular single-stranded nucleic acid molecules. Each of the circular single-stranded nucleic acid molecules contains reverse complementary strand of another circular single-stranded nucleic acid molecule. In some cases, this method disclosed herein eliminates the duplex region of the target double-stranded nucleic acid molecule. Accordingly, one is able to separately package individual strands of a double-stranded starting molecule into sequencing library constituents.

Some of these methods disclosed herein are compatible with any or all of paired-end read sequencing, indexing, and unique molecular index (UMI) barcoding.

Adapters

Provided herein are adapters for generating one or more circular nucleic acid molecules. Some of the adapters are Y adapters. Some of the Y adapters comprise at least part of an enzyme recognition nucleic acid molecule, a universal primer site, a surface binding site, and an index site. Some of the Y adapters further comprise a P5 site or a P7 site. One of the Y adapters contains both a region of two single stranded molecules (a fork region) and regions of self-complementary molecule. Some of the regions of self-complementary molecule comprise at least part of an enzyme recognition nucleic acid molecule, a universal primer site, a surface binding site, or an index site. Some of the fork regions comprise at least part of an enzyme recognition nucleic acid molecule, a universal primer site, a surface binding site, or an index site. The adapters, the universal primer site, the surface binding site, and the index site are described elsewhere herein.

In some cases, an enzyme binds to the enzyme recognition nucleic acid molecule. The enzyme cleaves the enzyme recognition nucleic acid molecule and, after the cleavage, rejoins cleavage ends of the enzyme recognition nucleic acid molecule. In some embodiments, the enzyme cleaves the enzyme recognition nucleic acid molecule and, after the cleavage, rejoins cleavage ends of the enzyme recognition nucleic acid molecule to form hairpin structures. One type of the enzyme is a protelomerase. One type of the protelomerase is TelN protelomerase. The TelN protelomerase is described elsewhere herein.

Some of the adapters are hairpin adapters. Some of the hairpin adapters comprise at least part of an enzyme recognition nucleic acid molecule, a universal primer site, a surface binding site, and an index site. Some of the hairpin adapters further comprise a P5 site or a P7 site. One of the hairpin adapters contains both a region of single stranded molecule (a loop region) and regions of self-complementary molecule. Some of the regions of self-complementary molecule comprise at least part of an enzyme recognition nucleic acid molecule, a universal primer site, a surface binding site, or an index site. Some of the loop regions comprise at least part of an enzyme recognition nucleic acid molecule, a universal primer site, a surface binding site, or an index site. The adapter, the universal primer site, the surface binding site, and the index site are described elsewhere herein.

In some cases, an enzyme binds to the enzyme recognition nucleic acid molecule. If the enzyme recognition nucleic acid molecule is in the regions of self-complementary molecule, the enzyme cleaves the enzyme recognition nucleic acid molecule and, after the cleavage, rejoins cleavage ends of the enzyme recognition nucleic acid molecule. In some embodiments, the enzyme cleaves the enzyme recognition nucleic acid molecule and, after the cleavage, rejoins cleavage ends of the enzyme recognition nucleic acid molecule to form hairpin structures. One type of the enzyme is a protelomerase. One type of the protelomerase is TelN protelomerase. The TelN protelomerase is described elsewhere herein.

Amplification

Some of the methods disclosed herein further comprise amplification of the plurality of circular nucleic acid molecules. Some of the amplifications comprise amplification by polymerase chain reaction (PCR), loop mediated isothermal amplification, nucleic acid sequence based amplification, strand displacement amplification, multiple displacement amplification, rolling circle amplification, ligase chain reaction, helicase dependent amplification, ramification amplification method, or any combination thereof. One type of amplification is clonal amplification of the plurality of circular nucleic acid molecules. One of the clonal amplification comprises performing rolling circle amplification. In some cases, the amplification comprises at least 2, 3, 4, 5, 6, 7, 8, 9, 10, 11, 12, 13 or greater cycles of amplification.

Any amplification method described herein optionally comprises repeated cycles of nucleic acid amplification. A cycle of amplification optionally comprises: (a) hybridization of one or more primers to a template strand or a complement thereof, (b) primer extension to form a first and/or second extended strand, and (c) partial or incomplete denaturation of the extended strand(s) from the template strand(s) or complements thereof, e.g., through the use of a non-thermal duplex destabilizing mechanism, such as the binding of a helicase or a single-stranded DNA binding protein, that shifts the equilibrium between single-stranded and double-stranded nucleic acid molecules towards the single-stranded form. One type of the template is a circular nucleic acid molecule.

Some of the circular nucleic acid molecules are amplified using primers. Some of the primers are supplied in solution or immobilized on a solid support. In some cases, the circular nucleic acid molecules are amplified using primers immobilized on/to one or more solid or semi-solid supports. In some cases, the support comprises immobilized primers that are complementary to a portion of an adapter in the circular nucleic acid molecule. In another example, the support optionally does not significantly comprise an immobilized primer that is complementary to a portion of an adapter in the circular nucleic acid molecule.

In some cases, a plurality of circular nucleic acid molecules are amplified simultaneously in a single continuous liquid phase in the presence of one or more supports, where each support comprises one or more immobilization sites. In some cases, each circular nucleic acid molecule is amplified to generate a clonal population of amplicons, where individual clonal populations are immobilized within or on a different immobilization site from other amplified populations. For example, a different immobilization site can be a different discrete region on a support. In some cases, the amplified populations remain substantially clonal after amplification.

A circular nucleic acid molecule is for example amplified to generate clonal populations which comprise both forward strand and reverse strand of a double-stranded nucleic acid molecule. In an embodiment, clonality is maintained in the resulting amplified nucleic acid populations by maintaining association between circular nucleic acid molecule and its primer immobilized, thereby effectively associating or "tethering" associated clonal progeny together and reducing the probability of cross-contamination between different clonal populations. In some cases, a clonal population of substantially identical nucleic acids has a spatially localized or discrete macroscopic appearance. In an embodiment, a clonal population resembles a distinct spot or colony.

Some of the methods generate a localized clonal population of clonal amplicons, optionally immobilized in/to/on one or more supports. One type of the support is solid or semisolid (such as a gel or hydrogel). The amplified clonal population is optionally attached to the support's external surface or can also be within the internal surfaces of a support (e.g., where the support has a porous or matrix structure).

In some cases, amplification is achieved by multiple cycles of primer extension along a circular nucleic acid molecule. In some cases, one or more primers are immobilized in/on/to one or more supports. In some cases, one primer is immobilized by attachment to a support. In some examples, a second primer is present and is optionally not immobilized or attached to a support. In some cases, different circular nucleic acid molecules are amplified onto different supports or immobilization sites simultaneously in a single continuous liquid phase to form clonal nucleic acid populations. One type of the liquid phase is considered continuous if any portion of the liquid phase is in fluid contact or communication with any other portion of the liquid body. In another example, a liquid phase is considered continuous if no portion is entirely subdivided or compartmentalized or otherwise entirely physically separated from the rest of the liquid body. In some cases, the liquid phase is flowable. In some cases, the continuous liquid phase is not within a gel or matrix. In other cases, the continuous liquid phase is within a gel or matrix. For example the continuous liquid phase occupies pores, spaces or other interstices of a solid or semisolid support.

Where the liquid phase is within a gel or matrix, one or more primers are immobilized on a support. In some cases, the support is the gel or matrix itself. Alternatively the support is not the gel or matrix itself. In an example one primer is immobilized on a solid support contained within a gel and is not immobilized to gel molecules. The support is for example in the form of a planar surface or one or more microparticles.

For some circular nucleic acid molecules, the first hybridization step comprises hybridizing a primer to the circular nucleic acid molecule for extension. For some circular nucleic acid molecules, the primer extension reaction comprises a step of rolling circle amplification (RCA) in which a strand-displacing polymerase synthesizes a new strand that is a concatemer comprising multiple copies of the nucleic acid molecule and adapter sequences encompassed by the circular nucleic acid molecules. In some cases, the concatemer contains at least one single strand (either forward or reverse strand) of the double-stranded target nucleic acid molecule. In some cases, the concatemer contains both strands (both forward and reverse strands) of the double-stranded target nucleic acid molecule. In some cases, the concatemer further comprises at least one enzyme recognition nucleic acid fragment. In yet another case, the concatemer further comprises at least one adapter between one enzyme recognition nucleic acid fragment and a single strand of the double-stranded target nucleic acid molecule. In some cases, the concatemer contains multiple single strands of the double-stranded target nucleic acid molecule, multiple enzyme recognition nucleic acid molecules, and multiple adapters between each enzyme recognition nucleic acid fragment and each single strand of the double-stranded target nucleic acid molecule. Some of the multiple adapters are separated by at least one single strand of the double-stranded target nucleic acid molecule or at least one enzyme recognition nucleic acid fragment.

In some cases, a given adapter of the multiple adapters comprises multiple surface binding sites, thereby binding to different immobilization sites on a surface. In this situation, the concatemer having the given adapter forms one or more bridge structures on the surface. Some of the bridge structures are then amplified through one or more application process.

Some of the methods are performed under isothermal amplification conditions. Some of the methods performed under isothermal amplification conditions use one or more non-thermal duplex destabilization mechanisms to promote primer hybridization and accelerate the amplification reactions under isothermal conditions. Examples of suitable non-thermal duplex destabilization mechanisms include, but are not limited to, (i) the use of chemical denaturants (e.g., NaOH solutions, high salt concentrations, etc.), (ii) the use of helicase proteins to facilitate the unwinding and separation of double-stranded regions of the nucleic acid molecules during the amplification reaction, (iii) the use of single-stranded DNA-binding proteins (SSBs) to shift the equilibrium between single-stranded and double-stranded nucleic acid molecules towards the single-stranded form during the amplification reaction, and (iv) the use of "thermal breathing" (i.e., fluctuations in the degree of nucleotide base-pairing when the reaction temperature is held fixed at or near the melting temperature, Tm, for duplex nucleic acid molecules). The destabilization of the duplex structure need only occur near the ends of the duplex molecule in order to facilitate primer binding and accelerate the amplification Some of the non-thermal duplex destabilization mechanisms employed comprise the use of at least one helicase, at least one single-stranded DNA binding protein, thermal breathing, or any combination thereof. Some of the methods use one of the non-thermal duplex destabilization mechanisms. Some of the methods use a combination of two or more non-thermal duplex destabilization mechanisms.

Some of the non-thermal duplex destabilization mechanisms allow the amplification process to be performed under isothermal conditions. As used herein, the term "isothermal" indicates that the set of amplification reactions may all be performed within a specified range of a specified set temperature. One type of the thermal breathing-dependent isothermal amplification is performed by maintaining the amplification reaction temperature to be within $\pm 1°$ C., $\pm 2.5°$ C., $\pm 5°$ C., $\pm 7.5°$ C., or $\pm 10°$ C. of a specified melting temperature for the circular nucleic acid molecule. One type of isothermal amplification is performed at a set temperature ranging from about 20° C. to about 80° C., or from about 20° C. to about 80° C. In some cases, the specified melting temperature is at least 20° C., at least 25° C., at least 30° C., at least 35° C., at least 40° C., at least 45° C., at least 50° C., at least 55° C., at least 60° C., at least 65° C., at least 70° C., at least 75° C., or at least 80° C. In some cases, the specified melting temperature is at most 80° C., at most 75° C., at most 70° C., at most 65° C., at most 60° C., at most 55° C., at most 50° C., at most 45° C., at most 40° C., at most 35° C., at most 30° C., at most 25° C., or at most 20° C.

Some of the methods for clonal amplification of nucleic acid molecules that comprise the use of one or more non-thermal duplex destabilization mechanisms enable one to achieve improved isothermal amplification rates such that the clonal population increases exponentially with a doubling time of at most 1 hour, 30 minutes, 20 minutes, 10 minutes, or 5 minutes or less. In other cases, the methods for clonal amplification of nucleic acid molecules that comprise the use of one or more non-thermal duplex destabilization mechanisms enable one to achieve improved isothermal amplification rates such that the clonal population increases exponentially with a doubling time of more than 1 hour.

Some of the methods for clonal amplification of nucleic acid molecules that comprise the use of one or more non-thermal duplex destabilization mechanisms enable one to achieve process times or isothermal amplification reaction times (i.e., the total time required to complete the clonal amplification process) of at most 50 minutes, 40 minutes, 30 minutes, 20 minutes, 10 minutes, or 5 minutes or less. In other cases, the methods for clonal amplification of nucleic acid molecules that comprise the use of one or more non-thermal duplex destabilization mechanisms enable one to achieve process times or isothermal amplification reaction times (i.e., the total time required to complete the clonal amplification process) of more than 50 minutes.

Some of the methods disclosed herein comprise sequencing the plurality of circular nucleic acid molecules. Such sequencing comprises bisulfite-free sequencing, bisulfite sequencing, TET-assisted bisulfite (TAB) sequencing, ACE-sequencing, high-throughput sequencing, Maxam-Gilbert sequencing, massively parallel signature sequencing, Polony sequencing, 454 pyrosequencing, Sanger sequencing, Illumina sequencing, SOLiD sequencing, Ion Torrent semiconductor sequencing, DNA nanoball sequencing, Heliscope single molecule sequencing, single molecule real time (SMRT) sequencing, nanopore DNA sequencing, shot gun sequencing, RNA sequencing, Enigma sequencing, or any combination thereof.

Some of the methods disclosed herein take at most about 5 hours, 4 hours, 3 hours, 2 hours, 1 hours, 30 minutes, 20 minutes, 10 minutes, 5 minutes or less to complete. In some cases, some of the methods disclosed herein take more than about 5 hours to complete. Some of the methods disclosed herein take from about 1 minute to 5 hours, 5 minutes to 4.5 hours, 10 minutes to 4 hours, 20 minutes to 3.5 hours, 30 minutes to 3 hours, 1 hour to 2.5 hour, or 1.5 hours to 2 hours to complete.

Some of the methods disclosed herein have higher efficiency to create nucleic acid libraries. Typical ligation based approaches cost 16 hours. Some of the methods disclosed herein take 30 minutes and are able to be optimized down to 5 minutes. Additionally, some of the methods disclosed herein create circular nucleic acid molecules to generate monoclonal, spatially resolved amplicons that demonstrate brighter signals during sequencing processes than circular nucleic acid molecules generated through ligation based approaches. Finally, some of the methods disclosed herein do not present complementary flanking sequencing or generate an entire complement to the library strand of interest that competes with amplification and inhibits amplicon growth.

Figure 5B:
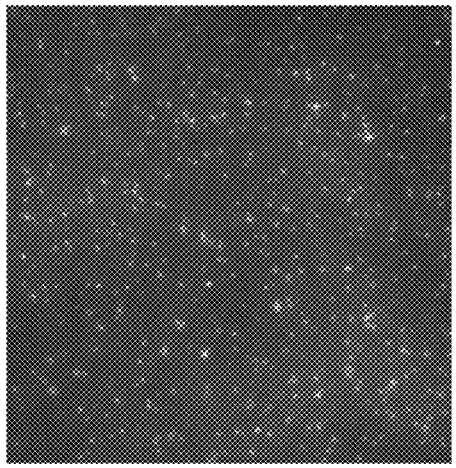
FIG. 5B depicts an example of sequencing signals generated by ligation based circulation.
Figure 5C:
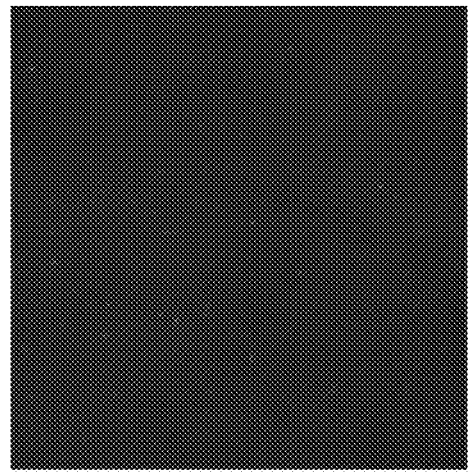
FIG. 5C depicts an example of sequencing signals generated by uncircularized library.
Figure 5A:
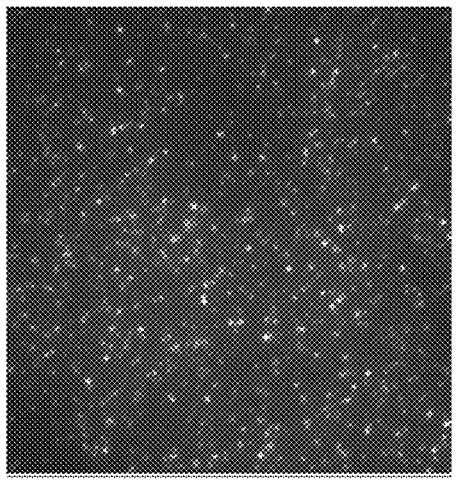
FIG. 5A depicts an example of sequencing signals generated by the method disclosed herein.

FIG. 5A depicts an example of sequencing signals generated by the method disclosed herein. FIG. 5B depicts an example of sequencing signals generated by ligation based circulation. FIG. 5C depicts an example of sequencing signals generated by uncircularized library. The circular nucleic acid library generated by methods disclosed herein demonstrates brighter signals with better signal to noise ratio compared to the library created by ligation based circulation or the uncircularized library.

Sequence

The TelN protelomerase comprises an amino acid sequence of SEQ ID NO: 1. Variants of this sequence, and enzymes having different sequence but comparable enzymatic activity or effecting comparable results when contacted to nucleic acids are also contemplated as consistent with and part of the disclosure herein. The SEQ ID NO:1 is MSKVKIGELINTLVNEVEAIDASDRPQGDKTKRI-KAAAARYKNALFNDKRKFRGKGLQKR ITANTFN AYMSRARKRFDDKLHHSFDKNINKLSEKYPLY-SEELSSWLSMPTANIRQHMSSL QSKLKEIMPLAEEL-SNVRIGSKGSDAKIARLIKKYPDWSFALSDLNSD DWKERRDYLYKLF QQGSALLEELHQLKVN-HEVLYHLQLSPAERTSIQQRWADVLREKKRNVV-VIDYPTYMQSI YDILNNPATLFSLNTRSGMAPLAFA-LAAVSGRRMIEIMFQGEFAVSGKYTVNFSGQAKKRS EDKSVTRTIYTLCEAKLFVELLTELRSCSAASDFD EVVKGYGKDDTRSENGRINAILAKAF NPWVKSF FGDDRRVYKDSRAIYARIAYEMFFRVDPRWKNVD-EDVFFMEILGHDDENTQL HYKQFKLANFSRTWRPE-VGDENTRLVALQKLDDEMPGFARGDAGVRL-HETVKQLVEQDP SAKITNSTLRAFKFSPTMISRYL EFAADALGQFVGENGQWQLKIETPAIVLPDEES-VETIDEP DDES QDDELDEDEIELDEGGGDEPTEEEG-PEEHQPTALKPVFKPAKNNGDGTYKIEFEYDG KHYAWSGPADSPMAAMRSAWETYYS*

Detection Methods

In some embodiments, sequencing methods utilizing the compositions and methods disclosed herein may incorporate a detection method enabling basecalling to reveal the sequence of the target nucleic acid. In some embodiments, these detection methods may include any method as is or may be known in the art of nucleic acid detection and/or nucleic acid sequencing. In some embodiments, said detection methods may include, for example, one or more of fluorescence detection, colorimetric detection, luminescence (such as chemiluminescence of bioluminescence) detection, interferometric detection, resonance-based detection such as raman detection, spin resonance-based detection, NMR-based detection, and the like, and other methods such as electrical detection, such as, for example, capacitance-based detection, impedance based detection, or electrochemical detection, such as detection of electrons generated by or within a chemical reaction, or combinations of electrical, such as, e.g., impedance measurements, with other, e.g., optical measurements.

Hybridization Buffers

In some embodiments, the methods and compositions as disclosed herein may comprise or may further comprise the use of one or more hybridization buffers. Said buffers may serve to, for example, reduce the time required to hybridize one or more clusters or nucleic acid molecules to a surface or a surface-bound oligonucleotide, or a solution phase oligonucleotide, such as an adapter oligonucleotide, a capture oligonucleotide, a condenser oligonucleotide, or the like. Said hybridization buffers may or may also, in some embodiments, lead to improved condensation of nucleic acid clusters such as reduced cluster volume or cross section, reduced hybridization or clustering time, reduced preparation time, or the like. In some embodiments, a hybridization buffer may comprise one or more of an organic solvent, a buffer, and optionally, a polar aprotic solvent.

The organic solvent described herein can have a dielectric constant that is the same as or close to acetonitrile. The dielectric constant of the organic solvent can be in the range of about 20-60, about 25-55, about 25-50, about 25-45, about 25-40, about 30-50, about 30-45, or about 30-40. The dielectric constant of the organic solvent can be greater than 20, 25, 30, 35, or 40. The dielectric constant of the organic solvent can be lower than 30, 40, 45, 50, 55, or 60. The dielectric constant of the organic solvent can be about 35, 36, 37, 38, or 39.

Dielectric constant may be measured using a test capacitor according to methods known in the art. Representative polar aprotic solvents having a dielectric constant between 30 and 120 may include any such solvent as is known in the art or disclosed elsewhere herein. Such solvents may particularly include, but are not limited to, acetonitrile, diethylene glycol, N,N-dimethylacetamide, dimethyl formamide, dimethyl sulfoxide, ethylene glycol, formamide, hexamethylphosphoramide, glycerin, methanol, N-methyl-2-pyrrolidinone, nitrobenzene, or nitromethane.

The organic solvent described herein can have a polarity index that is the same as or close to acetonitrile. The polarity index of the organic solvent can be in the range of about 2-9, 2-8, 2-7, 2-6, 3-9, 3-8, 3-7, 3-6, 4-9, 4-8, 4-7, or 4-6. The polarity index of the organic solvent can be greater than about 2, 3, 4, 4.5, 5, 5.5, or 6. The polarity index of the organic solvent can be lower than about 4.5, 5, 5.5, 6, 6.5, 7, 7.5, 8, 8.5, 9, or 10. The polarity index of the organic solvent can be about 5.5, 5.6, 5.7, or 5.8.

The Snyder Polarity Index may be calculated according to the methods disclosed in Snyder, L. R., Journal of Chromatography A, 92(2):223-30 (1974), which is incorporated by reference herein in it its entirety. Representative polar aprotic solvents having a Snyder polarity index between 6.2 and 7.3 may include any such solvent as is known in the art or disclosed elsewhere herein. Such solvents may particularly include, but are not limited to, acetonitrile, dimethyl acetamide, dimethyl formamide, N-methyl pyrrolidone, N,N-dimethyl sulfoxide, methanol, or formamide.

Relative polarity may be determined according to the methods given in Reichardt, C., Solvents and Solvent Effects in Organic Chemistry, 3rd ed., 2003, which is incorporated herein by reference in its entirety, and especially with respect to its disclosure of polarities and methods of determining or assessing the same for solvents and solvent molecules. Representative polar aprotic solvents having a relative polarity between 0.44 and 0.82 may include any such solvent as is known in the art or disclosed elsewhere herein. Such solvents may particularly include, but are not limited to, dimethylsulfoxide, acetonitrile, 3-pentanol, 2-pentanol,2-butanol, Cyclohexanol, 1-octanol, 2-propanol, 1-heptanol, i-butanol, 1-hexanol, 1-pentanol, acetyl acetone, ethyl acetoacetate, 1-butanol, benzyl alcohol, 1-propanol, 2-aminoethanol, Ethanol, diethylene glycol, methanol, ethylene glycol, glycerin, or formamide.

The Solvent Polarity (ET(30)) may be calculated according to the methods disclosed in Reichardt, C., Molecular Interactions, Volume 3, Ratajczak, H. and Orville, W. J., Eds (1982), which is incorporated by reference herein in it its entirety.

Some examples of organic solvent include but are not limited to acetonitrile, dimethylformamide (DMF), dimethylsulfoxide (DMSO), acetanilide, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, ethylene glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Representative polar aprotic solvents having a solvent polarity between 44 and 60 may include any such solvent as is known in the art or disclosed elsewhere herein. Such solvents may particularly include, but are not limited to, dimethyl sulfoxide, 2-methoxycarbonylphenol, triethyl phosphite, 3-pentanol, acetonitrile, nitromethane, cyclohexanol, 2-pentanol, 4-methyl-1,3, dioxolan-2-one, propylene carbonate, acrylonitrile, 1-phenylethanol, 1-dodecanol, 2-butanol, 2-methylcyclohexanol, 2,6, dimethylphenol, 2,6-xylenol, 1-decanol, cyclopentanol, dimethyl sulfone, 1-octanoldiethylene glycol mono n-butyl ether, butyl digol, 1-heptanol, 3-phenyl-1-propanol, 1,3-dioxolane-2-one, ethylene carbonate, 1-hexanol, 4-chlorobutyronitrile, 5-methyl-2-isopropylphenol, thymol, 3,5,5-trimethyl-1-hexanol, 3-methyl-1-butanol, isoamyl alcohol, 2-methyl-1-propanol, isobutyl alcohol, 2-(tert-butyl)phenol, 1-pentanol, 2-phenylethanol, 2-methylpentane-2,4-diol, dipropylene glycol, 2-isopropylphenol, 2-n-butoxyethanol, ethylene glycol mono-n-butyl ether, 1-butanol, 2-hydroxymethyl-tetrahydrofuran, tetrahydrofurfuryl alcohol, 2-hydroxymethylfuran, furfuryl alcohol, 1-propanol, 2,4-dimethylphenol, 2,4-xylenol, benzyl alcohol, 2-ethoxyphenol, 2-ethoxyethanol, 1,5-pentanediol, 1-bromo-2-propanol, 2-methyl-5-isopropylphenol, carvacrol, 2-aminoethanol, ethanol, n-methylacetamide, 3-chloropropionitrile, 2-propen-1-ol, allyl alcohol, 2-methoxy ethanol, 2-methylphenol, o-cresol, 1,3-butanediol, 2-propyn-1-ol, propargyl alcohol, 3-methylphenol, m-cresol, triethylene glycol, diethylene glycol, n-methylformamide, 1,2-propanediol, 1,3-propanediol, 2-chlorophenol, methanol, 1,2-ethanediol, glycol, formamide, 2,2,2-trichloroethanol, 1,2,3-propanetriol, glycerol, 2,2,3,3-tetrafluoro-1-propanol, 2,2,2-trifluoroethanol, 4-n-butylphenol, 4-methylphenol, or p-cresol.

Representative polar aprotic solvents having a dielectric constant in the range of about 30-115 may include any such solvent as is known in the art or disclosed elsewhere herein. Such solvents may particularly include, but are not limited to, dimethyl sulfoxide, 2-methoxycarbonylphenol, triethyl phosphite, 3-pentanol, acetonitrile, nitromethane, cyclohexanol, 2-pentanol, 4-methyl-1,3, dioxolan-2-one, propylene carbonate, acrylonitrile, 1-phenylethanol, 1-dodecanol, 2-butanol, 2-methylcyclohexanol, 2,6,dimethylphenol, 2,6-xylenol, 1-decanol, cyclopentanol, dimethyl sulfone, 1-octanoldiethylene glycol mono n-butyl ether, butyl digol, 1-heptanol, 3-phenyl-1-propanol, 1,3-dioxolane-2-one, ethylene carbonate, 1-hexanol, 4-chlorobutyronitrile, 5-methyl-2-isopropylphenol, thymol, 3,5,5-trimethyl-1-hexanol, 3-methyl-1-butanol, isoamyl alcohol, 2-methyl-1-propanol, isobutyl alcohol, 2-(tert-butyl)phenol, 1-pentanol, 2-phenylethanol, 2-methylpentane-2,4-diol, dipropylene glycol, 2-isopropylphenol, 2-n-butoxyethanol, ethylene glycol mono-n-butyl ether, 1-butanol, 2-hydroxymethyl-tetrahydrofuran, tetrahydrofurfuryl alcohol, 2-hydroxymethylfuran, furfuryl alcohol, 1-propanol, 2,4-dimethylphenol, 2,4-xylenol, benzyl alcohol, 2-ethoxyphenol, 2-ethoxyethanol, 1,5-pentanediol, 1-bromo-2-propanol, 2-methyl-5-isopropylphenol, carvacrol, 2-aminoethanol, ethanol, n-methylacetamide, 3-chloropropionitrile, 2-propen-1-ol, allyl alcohol, 2-methoxyethanol, 2-methylphenol, o-cresol, 1,3-butanediol, 2-propyn-1-ol, propargyl alcohol, 3-methylphenol, m-cresol, triethylene glycol, diethylene glycol, n-methylformamide, 1,2-propanediol, 1,3-propanediol, 2-chlorophenol, methanol, 1,2-ethanediol, glycol, formamide, 2,2,2-trichloroethanol, 1,2,3-propanetriol, glycerol, 2,2,3,3-tetrafluoro-1-propanol, 2,2,2-trifluoroethanol, 4-n-butylphenol, 4-methylphenol, or p-cresol.

Organic solvent addition: In some instances, the disclosed hybridization buffer formulations may include the addition of an organic solvent. Examples of suitable solvents include, but are not limited to, acetonitrile, ethanol, DMF, and methanol, or any combination thereof at varying percentages (typically >5%). In some instances, the percentage of organic solvent (by volume) included in the hybridization buffer may range from about 1% to about 20%. In some instances, the percentage by volume of organic solvent may be at least 1%, at least 2%, at least 3%, at least 4%, at least 5%, at least 6%, at least 7%, at least 8%, at least 9%, at least 10%, at least 15%, or at least 20%. In some instances, the percentage by volume of organic solvent may be at most 20%, at most 15%, at most 10%, at most 9%, at most 8%, at most 7%, at most 6%, at most 5%, at most 4%, at most 3%, at most 2%, or at most 1%. Any of the lower and upper values described in this paragraph may be combined to form a range included within the present disclosure, for example, the percentage by volume of organic solvent may range from about 4% to about 15%. Those of skill in the art will recognize that the percentage by volume of organic solvent may have any value within this range, e.g., about 7.5%.

When the organic solvent comprises a polar aprotic solvent, the amount of the polar aprotic solvent may be present in an amount effective to denature a double stranded nucleic acid. In some embodiments, the amount of the polar aprotic solvent is greater than about 10% by volume based on the total volume of the formulation. The amount of the polar aprotic solvent is about or more than about 5%, 10%, 15%, 20%, 25%, 30%, 35%, 40%, 50%, 60%, 70%, 80%, 90%, or higher, by volume based on the total volume of the formulation. The amount of the polar aprotic solvent is lower than about 15%, 20%, 25%, 30%, 35%, 40%, 50%, 60%, 70%, 80%, 90%, or higher, by volume based on the total volume of the formulation. In some embodiments, the amount of the polar aprotic solvent is in the range of about 10% to 90% by volume based on the total volume of the formulation. In some embodiments, the amount of the polar aprotic solvent is in the range of about 25% to 75% by volume based on the total volume of the formulation. In some embodiments, the amount of the polar aprotic solvent is in the range of about 10% to 95%, 10% to 85%, 20% to 90%, 20% to 80%, 20% to 75%, or 30% to 60% by volume based on the total volume of the formulation. In some embodiments, the polar aprotic solvent is formamide.

When the organic solvent comprises a polar aprotic solvent, the amount of the aprotic solvent may be present in an amount effective to denature a double stranded nucleic acid. In some embodiments, the amount of the aprotic solvent is greater than about 10% by volume based on the total volume of the formulation. The amount of the aprotic solvent is about or more than about 5%, 10%, 15%, 20%, 25%, 30%, 35%, 40%, 50%, 60%, 70%, 80%, 90%, or higher, by volume based on the total volume of the formulation. The amount of the aprotic solvent is lower than about 15%, 20%, 25%, 30%, 35%, 40%, 50%, 60%, 70%, 80%, 90%, or higher, by volume based on the total volume of the formulation. In some embodiments, the amount of the aprotic solvent solvent is in the range of about 10% to 90% by volume based on the total volume of the formulation. In some embodiments, the amount of the aprotic solvent solvent is in the range of about 25% to 75% by volume based on the total volume of the formulation. In some embodiments, the amount of the aprotic solvent solvent is in the range of about 10% to 95%, 10% to 85%, 20% to 90%, 20% to 80%, 20% to 75%, or 30% to 60% by volume based on the total volume of the formulation.

The composition described herein can include one or more crowding agents enhances molecular crowding. The crowding agent can be selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and combination thereof. A preferred crowding agent may comprise one or more of polyethylene glycol (PEG), dextran, proteins, such as ovalbumin or hemoglobin, or Ficoll.

A suitable amount of a crowding agent in the composition allows for, enhances, or facilitates molecular crowding. The amount of the crowding agent is about or more than about 1%, 2%, 3%, 5%, 10%, 15%, 20%, 25%, 30%, 35%, 40%, 50%, 60%, or higher, by volume based on the total volume of the formulation. In some cases, the amount of the molecular crowding agent is greater than 5% by volume based on the total volume of the formulation. The amount of the crowding agent is lower than about 3%, 5%, 10%, 12.5%, 15%, 20%, 25%, 30%, 35%, 40%, 50%, 60%, 70%, 80%, 90%, or higher, by volume based on the total volume of the formulation. In some cases, the amount of the molecular crowding agent can be less than 30% by volume based on the total volume of the formulation. In some embodiments, the amount of the organic solvent is in the range of about 25% to 75% by volume based on the total volume of the formulation. In some embodiments, the amount of the organic solvent is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some cases, the amount of the molecular crowding agent can be in the range of about 5% to about 20% by volume based on the total volume of the formulation. In some embodiments, the amount of the crowding agent is in the range of about 1% to 30% by volume based on the total volume of the formulation.

One example of the crowding agent in the composition is polyethylene glycol (PEG. In some embodiments, the PEG used can have a molecular weight sufficient to enhance or facilitate molecular crowding. In some embodiments, the PEG used in the composition has a molecular weight in the range of about 5 k-50 kDa. In some embodiments, the PEG used in the composition has a molecular weight in the range of about 10 k-40 kDa. In some embodiments, the PEG used in the composition has a molecular weight in the range of about 10 k-30 kDa. In some embodiments, the PEG used in the composition has a molecular weight in the range of about 20 kDa.

In some instances, the disclosed hybridization buffer formulations may include the addition of a molecular crowding or volume exclusion agent. Molecular crowding or volume exclusion agents are typically macromolecules (e.g., proteins) which, when added to a solution in high concentrations, may alter the properties of other molecules in solution by reducing the volume of solvent available to the other molecules. In some instances, the percentage by volume of molecular crowding or volume exclusion agent included in the hybridization buffer formulation may range from about 1% to about 50%. In some instances, the percentage by volume of molecular crowding or volume exclusion agent may be at least 1%, at least 5%, at least 10%, at least 15%, at least 20%, at least 25%, at least 30%, at least 35%, at least 40%, at least 45%, or at least 50%. In some instances, the percentage by volume of molecular crowding or volume exclusion agent may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of molecular crowding or volume exclusion agent may range from about 5% to about 35%. Those of skill in the art will recognize that the percentage by volume of molecular crowding or volume exclusion agent may have any value within this range, e.g., about 12.5%.

The compositions described herein may include pH buffer system that maintains the pH of the compositions in a range suitable for hybridization process. The pH buffer system can include one or more buffering agents selected from the group consisting of Tris, HEPES, TAPS, Tricine, Bicine, Bis-Tris, NaOH, KOH, TES, EPPS, MES, and MOPS. The pH buffer system can further include a solvent. A preferred pH buffer system includes MOPS, MES, TAPS, phosphate buffer combined with methanol, acetonitrile, ethanol, isopropanol, butanol, t-butyl alcohol, DMF, DMSO, or any combination therein The amount of the pH buffer system is effective to maintain the pH of the formulation to be in a range suitable for the hybridization. In some instances, the pH may be at least 3, at least 4, at least 5, at least 6, at least 7, at least 8, at least 9, or at least 10. In some instances, the pH may be at most 10, at most 9, at most 8, at most 7, at most 6, at most 5, at most 4, or at most 3. Any of the lower and upper values described in this paragraph may be combined to form a range included within the present disclosure, for example, the pH of the hybridization buffer may range from about 4 to about 8. Those of skill in the art will recognize that the pH of the hybridization buffer may have any value within this range, e.g., about pH 7.8. In some cases, the pH range is about 3 to about 10. In some instances, the disclosed hybridization buffer formulations may include adjustment of pH over the range of about pH 3 to pH 10, with a preferred buffer range of 5-9.

Additives that impact DNA melting temperatures: The compositions described herein can include one or more additives to allow for better control of the melting temperature of the nucleic acid and enhance the stringency control of the hybridization reaction. Hybridization reactions are usually carried out under the stringent conditions in order to achieve hybridization specificity. In some cases, the additive for controlling melting temperature of nucleic acid is formamide.

The amount of the additive for controlling melting temperature of nucleic acid can vary depending on other agents used in the compositions. The amount of the additive for controlling melting temperature of the nucleic acid is about or more than about 1%, 2%, 3%, 5%, 10%, 15%, 20%, 25%, 30%, 35%, 40%, 50%, 60%, or higher, by volume based on the total volume of the formulation. In some cases, the amount of the additive for controlling melting temperature of the nucleic acid is greater than about 2% by volume based on the total volume of the formulation. In some cases, the amount of the additive for controlling melting temperature of the nucleic acid is greater than 5% by volume based on the total volume of the formulation. In some cases, the amount of the additive for controlling melting temperature of the nucleic acid is lower than about 3%, 5%, 10%, 12.5%, 15%, 20%, 25%, 30%, 35%, 40%, 50%, 60%, 70%, 80%, 90%, or higher, by volume based on the total volume of the formulation. In some embodiments, the amount of the additive for controlling melting temperature of the nucleic acid is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some embodiments, the amount of the additive for controlling melting temperature of the nucleic acid is in the range of about 2% to 20% by volume based on the total volume of the formulation. In some cases, the amount of the additive for controlling melting temperature of the nucleic acid is in the range of about 5% to 10% by volume based on the total volume of the formulation.

In some instances, the disclosed hybridization buffer formulations may include the addition of an additive that alters nucleic acid duplex melting temperature. Examples of suitable additives that may be used to alter nucleic acid melting temperature include, but are not limited to, Formamide. In some instances, the percentage by volume of a melting temperature additive included in the hybridization buffer formulation may range from about 1% to about 50%. In some instances, the percentage by volume of a melting temperature additive may be at least 1%, at least 5%, at least 10%, at least 15%, at least 20%, at least 25%, at least 30%, at least 35%, at least 40%, at least 45%, or at least 50%. In some instances, the percentage by volume of a melting temperature additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a melting temperature additive may range from about 10% to about 25%. Those of skill in the art will recognize that the percentage by volume of a melting temperature additive may have any value within this range, e.g., about 22.5%.

In some instances, the disclosed hybridization buffer formulations may include the addition of an additive that impacts nucleic acid hydration. Examples include, but are not limited to, betaine, urea, glycine betaine, or any combination thereof. In some instances, the percentage by volume of a hydration additive included in the hybridization buffer formulation may range from about 1% to about 50%. In some instances, the percentage by volume of a hydration additive may be at least 1%, at least 5%, at least 10%, at least 15%, at least 20%, at least 25%, at least 30%, at least 35%, at least 40%, at least 45%, or at least 50%. In some instances, the percentage by volume of a hydration additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a hydration additive may range from about 1% to about 30%. Those of skill in the art will recognize that the percentage by volume of a melting temperature additive may have any value within this range, e.g., about 6.5%.

Low-Binding Surfaces

In some embodiments, the methods and compositions disclosed herein may comprise or may further comprise a low non-specific binding surface that enable improved nucleic acid hybridization and amplification performance. In some embodiments, a low nonspecific binding surface may function in part to assist or to support further improvements in clustering performance, such as reduced cluster size, improved clustering efficiency, increased clustering density, etc. in addition to, in concert with, or as an integral part of the role of a low nonspecific binding surface in providing high CNR in images of nucleic acid bound surfaces. In general, the disclosed surface may comprise one or more layers of a covalently or non-covalently attached low-binding, chemical modification layers, e.g., silane layers, polymer films, and one or more covalently or non-covalently attached primer sequences that may be used for tethering single-stranded template oligonucleotides to the surface. In some instances, the formulation of the surface, e.g., the chemical composition of one or more layers, the coupling chemistry used to cross-link the one or more layers to the surface and/or to each other, and the total number of layers, may be varied such that non-specific binding of proteins, nucleic acid molecules, and other hybridization and amplification reaction components to the surface is minimized or reduced relative to a comparable monolayer. Often, the formulation of the surface may be varied such that non-specific hybridization on the surface is minimized or reduced relative to a comparable monolayer. The formulation of the surface may be varied such that non-specific amplification on the surface is minimized or reduced relative to a comparable monolayer. The formulation of the surface may be varied such that specific amplification rates and/or yields on the surface are maximized. Amplification levels suitable for detection are achieved in no more than 2, 3, 4, 5, 6, 7, 8, 9, 10, 15, or 30 amplification cycles in some cases disclosed herein.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions known to those of skill in the art, and may comprise any of a variety of materials known to those of skill in the art. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternately or in combination, the substrate surface may be patterned using, e.g., contact printing and/or ink-jet printing techniques. In some instances, an ordered array or random patter of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 50,000, 500,000, 1,000,000 or more discrete regions, or any intermediate number spanned by the range herein.

In order to achieve low nonspecific binding surfaces (also referred to herein as "low binding" or "passivated" surfaces), hydrophilic polymers may be nonspecifically adsorbed or covalently grafted to the substrate or support surface. Typically, passivation is performed utilizing poly (ethylene glycol) (PEG, also known as polyethylene oxide (PEO) or polyoxyethylene), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

As a result of the surface passivation techniques disclosed herein, proteins, nucleic acids, and other biomolecules do not "stick" to the substrates, that is, they exhibit low nonspecific binding (NSB). Examples are shown below using standard monolayer surface preparations with varying glass preparation conditions. Hydrophilic surface that have been passivated to achieve ultra-low NSB for proteins and nucleic acids require novel reaction conditions to improve primer deposition reaction efficiencies, hybridization performance, and induce effective amplification. All of these processes require oligonucleotide attachment and subsequent protein binding and delivery to a low binding surface. As described below, the combination of a new primer surface conjugation formulation (Cy3 oligonucleotide graft titration) and resulting ultra-low non-specific background (NSB functional tests performed using red and green fluorescent dyes) yielded results that demonstrate the viability of the disclosed approaches. Some surfaces disclosed herein exhibit a ratio of specific (e.g., hybridization to a tethered primer or probe) to nonspecific binding (e.g., Binter) of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal (e.g., for specifically-hybridized to nonspecifically bound labeled oligonucleotides, or for specifically-amplified to nonspecifically-bound (Binter) or non-specifically amplified (Bintra) labeled oligonucleotides or a combination thereof (Binter+Bintra)) for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In order to scale primer surface density and potentially to add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple steps.

The attachment chemistry used to graft a first chemically-modified layer to a support surface will generally be dependent on both the material from which the support is fabricated and the chemical nature of the layer. In some instances, the first layer may be covalently attached to the support surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid (H2SO4) and hydrogen peroxide (H2O2)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the support surface, where the choice of components used may be varied to alter one or more properties of the support surface, e.g., the surface density of functional groups and/or tethered oligonucleotide primers, the hydrophilicity/hydrophobicity of the support surface, or the three three-dimensional nature (i.e., "thickness") of the support surface. Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (-hydroxylethyl methacrylate) (branced PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a power of 2' number of branches, such as 2, 4, 8, 16, 32, 64, or 128 branches.

Exemplary PEG multilayers include PEG (8,16,8) on PEGamine-APTES, exposed to two layers of 7 uM primer pre-loading, exhibited a concentration of 2,000,000 to 10,000,000 on the surface. Similar concentrations were observed for 3-layer multi-arm PEG (8,16,8) and (8,64,8) on PEGamine-APTES exposed to 8 uM primer, and 3-layer multi-arm PEG (8,8,8) using star-shape PEG-amine to replace dumbbell-shaped 16 mer and 64 mer. PEG multilayers having comparable first, second and third PEG level are also contemplated.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some instances, e.g., wherein at least one layer of a multi-layered surface comprises a branched polymer, the number of covalent bonds between a branched polymer molecule of the layer being deposited and molecules of the previous layer may range from about one covalent linkages per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 or more than 32 covalent linkages per molecule.

Any reactive functional groups that remain following the coupling of a material layer to the support surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface of the disclosed low binding supports may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on and/or conjugated to the substrate surface using a polar protic solvent, a polar aprotic solvent, a nonpolar solvent, or any combination thereof. In some instances the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of an organic solvent. The pH of the solvent mixture used may be less than 5, 5, 5, 5, 6, 6, 6.5, 7, 7.5, 8, 8.5, 9, 9.5, 10, or greater than 10, or any value spanned or adjacent to the range described herein.

In some instances, one or more layers of low non-specific binding material may be deposited on and/or conjugated to the substrate surface using a mixture of organic solvents, wherein the dielectric constant of at least once component is less than 40 and constitutes at least 50% of the total mixture by volume. In some instances, the dielectric constant of the at least one component may be less than 10, less than 20, less than 30, less than 40. In some instances, the at least one component constitutes at least 20%, at least 30%, at least 40%, at least 50%, at least 50%, at least 60%, at least 70%, or at least 80% of the total mixture by volume.

As noted, the low non-specific binding supports of the present disclosure exhibit reduced non-specific binding of proteins, nucleic acids, and other components of the hybridization and/or ampltification formulation used for solid-phase nucleic acid amplification. The degree of non-specific binding exhibited by a given support surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low-binding supports of the present disclosure may exhibit non-specific protein binding (or non-specific binding of other specified molecules, e.g., Cy3 dye) of less than 0.001 molecule per µm2, less than 0.01 molecule per µm2, less than 0.1 molecule per µm2, less than 0.25 molecule per µm2, less than 0.5 molecule per µm2, less than 1molecule per µm2, less than 10 molecules per µm2, less than 100 molecules per µm2, or less than 1,000 molecules per µm2. Those of skill in the art will realize that a given support surface of the present disclosure may exhibit non-specific binding falling anywhere within this range, for example, of less than 86 molecules per µm2. For example, some modified surfaces disclosed herein exhibit nonspecific protein binding of less than 0.5 molecule/µm2 following contact with a 1 uM solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per um2. In independent nonspecific binding assays, 1 uM labeled Cy3 SA (ThermoFisher), 1 uM Cy5 SA dye (ThermoFisher), 10 uM Aminoallyl-dUTP-ATTO-647N (Jena Biosciences), 10 uM Aminoallyl-dUTP-ATTO-Rhol1 (Jena Biosciences), 10 uM Aminoallyl-dUTP-ATTO-Rhol1 (Jena Biosciences), 10 uM 7-Propargylamino-7-deaza-dGTP-Cy5 (Jena Biosciences, and 10 uM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon instrument using the Cy3, AF555, or Cy5 filter sets (according to dye test performed) as specified by the manufacturer at a PMT gain setting of 800 and resolution of 50-100 µm. For higher resolution imaging, images were collected on an Olympus IX83 microscope (Olympus Corp., Center Valley, PA) with a total internal reflectance fluorescence (TIRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75 W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per µm2.

In some instances, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some instances, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 30 degrees. In some instances, the water contact angle for the hydrophilic, low-binding support surfaced disclosed herein may no more than 50 degrees, 45 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding support surface of the present disclosure may exhibit a water contact angle having a value of anywhere within this range.

In some instances, the hydrophilic surfaces disclosed herein facilitate reduced wash times for bioassays, often due to reduced nonspecific binding of biomolecules to the low-binding surfaces. In some instances, adequate wash steps may be performed in less than 60, 50, 40, 30, 20, 15, 10, or less than 10 seconds. For example, in some instances adequate wash steps may be performed in less than 30 seconds.

Some low-binding surfaces of the present disclosure exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some instances, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some instances, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

Fluorescence excitation energies vary among particular fluorophores and protocols, and may range in excitation wavelength from less than 400 nm to over 800 nm, consistent with fluorophore selection or other parameters of use of a surface disclosed herein.

Accordingly, low background surfaces as disclosed herein exhibit low background fluorescence signals or high contrast to noise (CNR) ratios relative to known surfaces in the art. For example, in some instances, the background fluorescence of the surface at a location that is spatially distinct or removed from a labeled feature on the surface (e.g., a labeled spot, cluster, discrete region, sub-section, or subset of the surface) comprising a hybridized cluster of nucleic acid molecules, or a clonally-amplified cluster of nucleic acid molecules produced by 20 cycles of nucleic acid amplification via thermocycling, may be no more than 20×, 10×, 5×, 2×, 1×, 0.5×, 0.1×, or less than 0.1× greater than the background fluorescence measured at that same location prior to performing said hybridization or said 20 cycles of nucleic acid amplification.

In some instances, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

The surface that comprises the one or more chemically-modified layers, e.g., layers of a low non-specific binding polymer, may be independent or integrated into another structure or assembly. The chemical modification layers may be applied uniformly across the surface. Alternately, the surface may be patterned, such that the chemical modification layers are confined to one or more discrete regions of the substrate. For example, the surface may be patterned using photolithographic techniques to create an ordered array or random pattern of chemically-modified regions on the surface. Alternately or in combination, the substrate surface may be patterned using, e.g., contact printing and/or ink-jet printing techniques. In some instances, an ordered array or random patter of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In order to achieve low nonspecific binding surfaces (also referred to herein as "low binding" or "passivated" surfaces), hydrophilic polymers may be nonspecifically adsorbed or covalently grafted to the surface. Typically, passivation is performed utilizing poly(ethylene glycol) (PEG, also known as polyethylene oxide (PEO) or polyoxyethylene) or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In order to scale primer surface density and add additional dimensionality to hydrophilic or amphoteric surfaces, surfaces comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple steps.

The attachment chemistry used to graft a first chemically-modified layer to a surface will generally be dependent on both the material from which the surface is fabricated and the chemical nature of the layer. In some instances, the first layer may be covalently attached to the surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the surface. For example, glass or silicon surfaces may be acid-washed using a Piranha solution (a mixture of sulfuric acid (H2SO4) and hydrogen peroxide (H2O2)), base treatment in KOH and NaOH, and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the surface, where the choice of components used may be varied to alter one or more properties of the surface, e.g., the surface density of functional groups and/or tethered oligonucleotide primers, the hydrophilicity/hydrophobicity of the surface, or the three three-dimensional nature (i.e., "thickness") of the surface. Examples of preferred polymers that may be used to create one or more layers of low non-specific binding material in any of the disclosed surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly(N-isopropylacrylamide) (branched PNIPAM), branched poly(methyl methacrylate) (branched PMA), branched poly(-hydroxylethyl methacrylate) (branced PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some instances, e.g., wherein at least one layer of a multi-layered surface comprises a branched polymer, the number of covalent bonds between a branched polymer molecule of the layer being deposited and molecules of the previous layer may range from about one covalent linkages per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on and/or conjugated to the substrate surface using a polar protic solvent, an organic solvent, a nonpolar solvent, or any combination thereof. In some instances the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some instances, aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than 6, about 6, 6.5, 7, 7.5, 8, 8.5, 9, or greater than 9 mk.

As noted, the low non-specific binding surface exhibit reduced non-specific binding of nucleic acids, and other components of the hybridization and/or amplification formulation used for solid-phase nucleic acid amplification. The degree of non-specific binding exhibited by a given surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding surface comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on surfaces comprising different surface formulations—provided that care has been taken to ensure that the fluorescence imaging is performed under conditions where fluorescence signal is linearly related (or related in a predictable manner) to the number of fluorophores on the surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different surface formulations of the present disclosure.

As noted, in some instances, the degree of non-specific binding exhibited by the disclosed low-binding surfaces may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given surface formulation may thus be assessed in terms of the number of non-specifically bound protein molecules (or other molecules) per unit area. In some instances, the low-binding surfaces of the present disclosure may exhibit non-specific protein binding (or non-specific binding of other specified molecules, e.g., Cy3 dye) of less than 0.001 molecule per $\mu m2$, less than 0.01 molecule per $\mu m2$, less than 0.1 molecule per $\mu m2$, less than 0.25 molecule per $\mu m2$, less than 0.5 molecule per $\mu m2$, less than 1molecule per $\mu m2$, less than 10 molecules per $\mu m2$, less than 100 molecules per $\mu m2$, or less than 1,000 molecules per $\mu m2$. Those of skill in the art will realize that a given surface of the present disclosure may exhibit non-specific binding falling anywhere within this range, for example, of less than 86 molecules per $\mu m2$. For example, some modified surfaces disclosed herein exhibit nonspecific protein binding of less than 0.5 molecule/$\mu m2$ following contact with a 1 $\mu M$ solution of bovine serum albumin (BSA) in phosphate buffered saline (PBS) buffer for 30 minutes, followed by a 10 minute PBS rinse. Some modified surfaces disclosed herein exhibit nonspecific binding of Cy3 dye molecules of less than 0.25 molecules per $\mu m2$.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface)

to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding surfaces disclosed herein may range from about 0 degrees to about 30 degrees. In some instances, the water contact angle for the hydrophilic, low-binding surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. Those of skill in the art will realize that a given hydrophilic, low-binding surface of the present disclosure may exhibit a water contact angle having a value of anywhere within this range.

In some instances, the low-binding surfaces of the present disclosure may exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some instances, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some instances, the surfaces disclosed herein may exhibit a high ratio of specific signal to nonspecific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface. Accordingly, low background surfaces as disclosed herein exhibit low background fluorescence signals or high contrast to noise (CNR) ratios relative to known surfaces in the art.

In general, at least one layer of the one or more layers of low non-specific binding material may comprise functional groups for covalently or non-covalently attaching oligonucleotide adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one layer may be distributed at a plurality of depths throughout the layer.

One or more types of oligonucleotide primer may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the tethered primer sequences may comprise modifications designed to facilitate the specificity and efficiency of nucleic acid amplification as performed on low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

In some embodiments, it may be desirable to vary the surface density of tethered primers on the support surface and/or the spacing of the tethered primers away from the support surface (e.g., by varying the length of a linker molecule used to tether the primers to the surface) in order to "tune" the support for optimal performance when using a given amplification method. As noted below, adjusting the surface density of tethered primers may impact the level of specific and/or non-specific amplification observed on the support in a manner that varies according to the amplification method selected. In some instances, the surface density of tethered oligonucleotide primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radioisotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the resultant surface density of oligonucleotide primers on the low binding support surfaces of the present disclosure may range from about 1,000 primer molecules per μm2 to about 100,000 primer molecules per μm2. In some instances, the surface density of oligonucleotide primers may be at least 1,000, at least 10,000, or at least 100,000, molecules per μm2. In some instances, the surface density of oligonucleotide primers may be at most 500,000, at most 100,000, at most 10,000, at most 1,000, or at most 100 molecules per μm2. Any of the lower and upper values described in this paragraph may be combined to form a range included within the present disclosure, for example, in some instances the surface density of primers may range from about 1,000 molecules per μm2 to about 10,000 molecules per μm2. Those of skill in the art will recognize that the surface density of primer molecules may have any value within this range, e.g., about 4,000 or about 5,000 molecules per μm2. In some instances, the surface density of template library nucleic acid sequences initially hybridized to adapter or primer sequences on the support surface may be less than or equal to that indicated for the surface density of tethered oligonucleotide primers. In some instances, the surface density of clonally-amplified template library nucleic acid sequences hybridized to adapter or primer sequences on the support surface may span the same range as that indicated for the surface density of tethered oligonucleotide primers. In some instances, the surface density of clonally-amplified template library nucleic acid sequences hybridized to adapter or primer sequences on the support surface may be less than that indicated for the surface density of tethered oligonucleotide primers.

Local densities as listed above do not preclude variation in density across a surface, such that a surface may comprise a region having an oligo density of, for example, 500, 5,000, 50,000/μm2, or more, while also comprising at least a second region having a substantially different local density.

In some instances, the use of the buffer formulations disclosed herein (optionally, used in combination with low non-specific binding surface) yield relative hybridization rates that range from about 2× to about 20× faster than that for a conventional hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, or at least 20× that for a conventional hybridization protocol.

The method and composition described herein can help shorten the time required for completing the hybridization step. In some embodiments, the hybridization time can be in the range of about 1 s to 2 h, about 5 s to 1.5 h, about 15 s to 1 h, or about 15 s to 0.5 h. In some embodiments, the hybridization time can be in the range of about 15 s to 1 h. In some embodiments, the hybridization time can be shorter than 15 s, 30 s, 1 min, 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, the hybridization time can be longer than 1 s, 5 s, 10 s, 15 s, 30 s, 1 min, 1.5 min, 2 min, 2.5 min, 3 min, 4 min, or 5 min.

The annealing methods described herein can significantly shorten the annealing time. In some embodiments, at least 90% of the target nucleic acid anneals to the surface bound nucleic acid in less than 15 s, 30 s, 1 min, 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, at least 80% of the target nucleic acid anneals to the surface bound nucleic acid in less than 15 s, 30 s, 1 min, 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, at least 90% of the target nucleic acid anneals to the surface bound nucleic acid in greater than 1 s, 5 s, 10 s, 15 s, 30 s, 1 min, 1.5 min, 2 min, 2.5 min, 3 min, 4 min, or 5 min. In some embodiments, at least 90% of the target nucleic acid anneals to the surface bound nucleic acid in the range of about 10 s to about 1 hour, about 30 s to about 50 min, about 1min to about 50 min, or about 1min to about 30 min.

Improvements in hybridization efficiency: As used herein, hybridization efficiency (or yield) is a measure of the percentage of total available surface-tethered adapter sequences, nontethered adapter sequences, condenser sequences, primer sequences, oligonucleotide sequences, or other sequences that are hybridized to complementary sequences. In some instances, the use of optimized buffer formulations disclosed herein (optionally, used in combination with low non-specific binding surface) yield improved hybridization efficiency compared to that for a conventional hybridization protocol. In some instances, the hybridization efficiency that may be achieved is better than 80%, 85%, 90%, 95%, 98%, or 99% in any of the hybridization reaction times specified above.

The methods and compositions described herein can be used in an isothermal annealing conditions. In some embodiments, one or more of the methods described herein can eliminate the cooling step required for most hybridization steps. In some embodiments, the annealing methods described herein can be performed at a temperature in the range of about 10° C. to 95° C., about 20° C. to 80° C., about 30° C. to 70° C. In some embodiments, the temperature can be lower than about 40° C., 50° C., 60° C., 70° C., 80° C., or 90° C.

As used herein, hybridization specificity is a measure of the ability of tethered adapter sequences, primer sequences, or oligonucleotide sequences in general to correctly hybridize only to completely complementary sequences. In some instances, the use of the optimized buffer formulations disclosed herein (optionally, used in combination with low non-specific binding surface) yield improved hybridization specificity compared to that for a conventional hybridization protocol. In some instances, the hybridization specificity that may be achieved is better than 1 base mismatch in 10 hybridization events, 1 base mismatch in 100 hybridization events, 1 base mismatch in 1,000 hybridization events, or 1 base mismatch in 10,000 hybridization events.

Computer Control Systems

Figure 6:
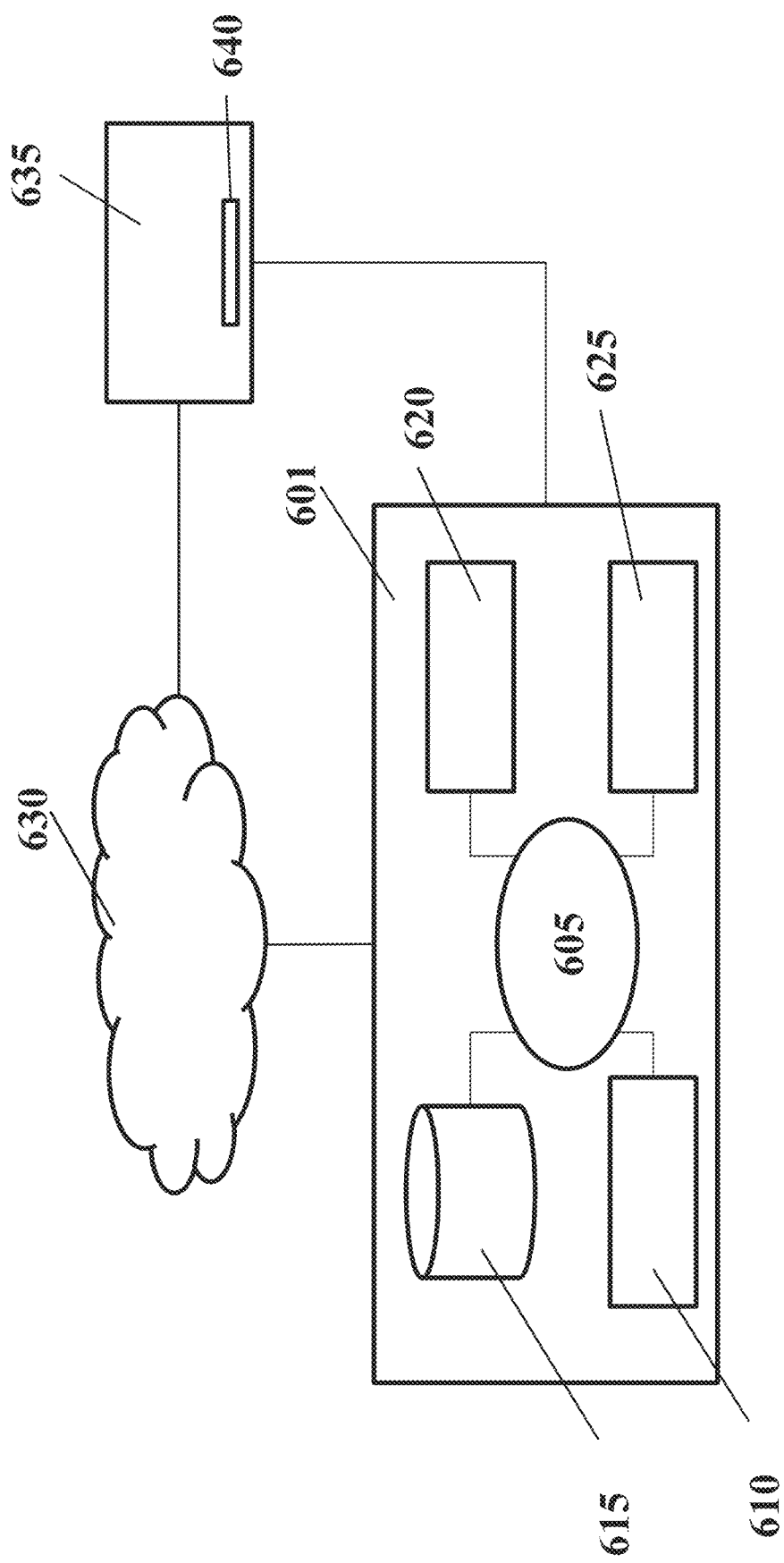
FIG. 6 shows a computer control system that is programmed or otherwise configured to implement methods provided herein.

The present disclosure provides computer control systems that are programmed to implement methods of the disclosure. FIG. 6 shows a computer system 601 that is programmed or otherwise configured to implement methods of the disclosure. The computer system 601 can regulate various aspects of the present disclosure, such as, for example, controlling the experiment conditions of generating the circular nucleic acid molecule, analyzing the target nucleic acid molecule, and optimizing the experiment conditions of generating the circular nucleic acid library. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, parameters of on-going experiments, and information regarding the nucleic acid sequencing. Examples of UI's include, without limitation, a graphical user interface (GUI) and web-based user interface.

Methods of the present disclosure can be implemented by way of one or more algorithms. An algorithm can be implemented by way of software upon execution by the central processing unit 605. The algorithm can, for example, analyze big sequence data and simulate biochemical reaction networks.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

What is claimed is:

1. A method for determining a sequence, comprising:
   (a) providing a concatemer, wherein said concatemer comprises (i) an adapter sequence configured to couple to a single surface-bound oligonucleotide and (ii) a strand comprising two or more repeats of an identical sequence, and wherein said two or more repeats of said identical sequence comprise a target sequence and an enzyme recognition site;
   (b) coupling said concatemer to a surface;
   (c) hybridizing a primer sequence complementary to said target sequence, thereby producing a primed nucleic acid sequence;
   (d) extending said primed nucleic acid sequence;
   (e) digesting said strand;
   (f) hybridizing another primer sequence to another target sequence in another strand of said concatemer, wherein said another strand is complementary to said strand, thereby producing another primed nucleic acid sequence, and wherein said strand and said another strand are formed by rolling circle amplification (RCA) and multiple displacement amplification (MDA); and
   (g) extending said another primed nucleic acid sequence.

2. The method of claim 1, wherein said target sequence and said another target sequence are different.

3. The method of claim 1, further wherein said another strand is generated from said strand, optionally, wherein a generation of said another strand from said strand comprises using a primer that hybridizes to said target sequence of said strand.

4. The method of claim 1, wherein step (a) further comprises:
   (i) providing a support comprising an immobilized primer;
   (ii) hybridizing a nucleic acid to said immobilized primer; and
   (iii) performing a rolling circle amplification to extend said immobilized primer along said nucleic acid to generate said strand.

5. The method of claim 4, further comprising generating said another strand using another immobilized primer that binds to a primer binding site of said strand.

6. The method of claim 5, wherein said target sequence is different from said primer binding site.

7. The method of claim 1, wherein said concatemer is a circular nucleic acid template.

8. The method of claim 4, further comprising circularizing said concatemer prior to step (a)(iii).

9. The method of claim 1, wherein said strand is generated from a nucleic acid template with isothermal amplification, further wherein said isothermal amplification is a rolling circle amplification.

10. The method of claim 1, wherein a first portion of said target sequence is determined from said strand and a second portion of said target sequence is determined from said other strand.

11. The method of claim 1, wherein said strand comprises one or more nucleotides that are modified or one or more nucleotides with bases that are modified.

12. The method of claim 11, wherein said one or more nucleotides that are modified or said one or more nucleotides with said bases that are modified comprise non-canonical nucleotides.

13. The method of claim 12, wherein said strand is generated by extending an immobilized primer in a presence of deoxyribonucleotide triphosphates comprising dATP, dTTP, dGTP, dCTP, and a modified or non-canonical deoxyribonucleotide triphosphate, optionally wherein said non-canonical deoxyribonucleotide trisphosphate is dUTP.

14. The method of claim 1, wherein said concatemer further comprises one or more unique molecular identifiers (UMI).

15. The method of claim 1, wherein said concatemer has a length comprising between about 100 and about 5,000 nucleotides.

16. The method of claim 1, wherein said concatemer has a length comprising at least about 10 nucleotides.

17. A method for determining a sequence, comprising:
(a) digesting a strand of a concatemer attached to a solid support, wherein said concatemer comprises a strand comprising two or more repeats of an identical sequence, and wherein said two or more identical sequences comprise a target sequence and an enzyme recognition site;
(b) hybridizing a primer sequence to another target sequence in another strand of said concatemer, wherein said another strand is complementary to said strand, thereby producing another primed nucleic acid sequence; and
(c) extending said another primed nucleic acid sequence.

18. The method of claim 17, further comprising determining said target sequence of at least a portion of said strand prior to said digesting said strand of (a).

19. The method of claim 17, wherein said concatemer is a circular nucleic acid template.

20. The method of claim 19, further comprising circularizing said concatemer.

* * * * *